United States Patent
DeLuca et al.

(10) Patent No.: US 8,193,171 B2
(45) Date of Patent: Jun. 5, 2012

(54) **13,13-DIMETHYL-*DES*-C,D ANALOGS OF 1α,25-DIHYDROXY-19-NOR-VITAMIN D₃ COMPOUNDS AND TOPICAL COMPOSITION DOSAGE FORMS AND METHODS OF TREATING SKIN CONDITIONS THEREOF**

(75) Inventors: Hector F. DeLuca, Deerfield, WI (US); Margaret Clagett-Dame, Deerfield, WI (US); Lori A. Plum, Arena, WI (US); Rafal R. Sicinski, Warsaw (PL); Katarzyna Plonska-Ocypa, Warsaw (PL); Nirca J. Nieves, Madison, WI (US); Pawel Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/357,702

(22) Filed: Jan. 22, 2009

(65) Prior Publication Data

US 2009/0186950 A1 Jul. 23, 2009

Related U.S. Application Data

(60) Provisional application No. 61/022,696, filed on Jan. 22, 2008.

(51) Int. Cl.
*A61K 31/047* (2006.01)
*C07C 35/17* (2006.01)
*C07C 401/00* (2006.01)
*A61P 17/00* (2006.01)

(52) U.S. Cl. ........................... 514/167; 552/653
(58) Field of Classification Search ............. 514/167; 552/653
See application file for complete search history.

(56) References Cited

U.S. PATENT DOCUMENTS

| | | | |
|---|---|---|---|
| 5,086,191 A | 2/1992 | DeLuca et al. |
| 5,536,713 A | 7/1996 | Deluca et al. |
| 5,843,928 A | 12/1998 | Deluca et al. |
| 5,936,133 A | 8/1999 | Deluca et al. |
| 5,969,190 A | 10/1999 | Bauer et al. |
| 6,184,422 B1 | 2/2001 | Barbier et al. |

(Continued)

FOREIGN PATENT DOCUMENTS

WO 95/01960 * 1/1995

(Continued)

OTHER PUBLICATIONS

International Preliminary Report on Patentability for Intl. Pat. Appln. No. PCT/US2009/031663, dated Jul. 27, 2010.

(Continued)

*Primary Examiner* — Sabiha Qazi
(74) *Attorney, Agent, or Firm* — Joseph P. Meara; Foley & Lardner LLP

(57) ABSTRACT

13,13-Dimethyl-des-C,D analogs of 1α,25-dihydroxy-19-nor-vitamin D₃ compounds and topical composition dosage forms thereof, and methods of treating skin conditions thereof. Exemplary active pharmaceutical ingredients include (1R,3R)-5-[(E)-(S)-11'-hydroxy-5',5',7',11'-tetramethyl-dodec-2'-enylidene]-2-methylene-cyclohexane-1,3-diol, (1R,3R)-5-[(Z)-(S)-11'-hydroxy-5',5',7',11'-tetramethyl-dodec-2'-enylidene]-2-methylene-cyclohexane-1,3-diol, (1R,3R)-5-[(E)-(R)-11'-hydroxy-5',5',7',11'-tetramethyl-dodec-2'-enylidene]-2-methylene-cyclohexane-1,3-diol, and (1R,3R)-5-[(Z)-(R)-11'-hydroxy-5',5',7',11'-tetramethyl-dodec-2'-enylidene]-2-methylene-cyclohexane-1,3-diol.

37 Claims, 7 Drawing Sheets

U.S. PATENT DOCUMENTS

| | | | |
|---|---|---|---|
| 6,392,071 | B1 | 5/2002 | DeLuca et al. |
| 7,534,777 | B2 * | 5/2009 | DeLuca et al. ............... 514/167 |
| 2007/0112077 | A1 | 5/2007 | DeLuca et al. |

FOREIGN PATENT DOCUMENTS

| | | |
|---|---|---|
| WO | WO 98/52894 | 11/1998 |
| WO | WO 99/43646 | 9/1999 |
| WO | WO 2009/094426 | 7/2009 |

OTHER PUBLICATIONS

Office Action for Mexican Pat. Appln. No. MX/a/2010/007956, dated Oct. 31, 2011, 3 pp. and English summary in lieu of a translation, 1 page.

Baggiolini E et al., "Stereocontrolled total synthesisi of 1.alpha.,25-dihydroxycholecalciferol and 1.alpha.,25-dihydroxyergocalciferol," J. Org Chem., 1986, 51(16):3096-3108.

Bouclier M et al., "Experimental Models in Skin Pharmacology," Pharmacological Reviews, 1990, 42:127:154.

Collins S. J. et al., "Normal Functional Characteristics of Cultured Human Promyelocytic Leukemia Cells (HL-60) . . . ," J. Exper. Med, 1979, 149:969-974.

Greene T. and Wuts P., "Protective Groups in Organic Synthesis," John Wiley & Sons, Inc., 1999, pp. 17-200.

Hilpert H. and Wirz B., "Novel versatile approach to an enantiopure 19-nor,des-C,D vitamin D3 derivative," Tetrahedron, 2001, 51:681-694.

Kutner A. et al., "Synthesis of Retiferol RAD1 and RAD2, the Lead Representatives of a New Class of des-CD Analogs of Cholecalciferol," Bioorganic Chem., 1995, 23:22-32.

Lythgoe B. et al., "Calciferol and its Relatives," J. Chem. Soc. Perkin Trans. I, 1978, 590-595.

Lythgoe B., "Synthetic approaches to Vitamin D and its Relatives," Chem. Soc. Rev. 9, 449-475, 1980.

Ostrem, V. K. et al., "24- and 26-homo-1,25-dihydroxyvitamin D3: Preferential activity in inducing differentiation . . . ," Proc. Natl. Acad. Sci. USA, 1987, 84:2610-2614.

Perlman K. L. et al., "1alpha,25-Dihydroxy-19-NOR-Vitamin D3, A Novel Vitamin D-Related Compound with Potential Therapeutic Activity," Tetrhedron, 1990, 31(13):1823-1824.

Perlman K. L. et al., "Novel Synthesis of 19-NOR-Vitamin D Compounds," Tetrahedron, 1991, 32(52):7663-7666.

Sardina F. J. et al., "Studies on the synthesis of side-chain hydroxylated metabolites of vitamin D. 2. Stereocontrolled synthesis . . . ," J. Org. Chem, 1986, 51(8)1264-1269.

Sicinski R. R. et al., "New 1alpha,25-Dihydroxy-19-norvitamin D Compounds of High Biological Activity: Synthesis and Biological Evaluation . . . ,"J. Med. Chem, 1998, 41:4662-4674.

Sicinski R. R. et al., "New highly calcemic 1alpha,25-dihydroxy-19-norvitamin D3 compounds with modified side chain: 26,27-dimethylene . . . ," Steroids, 2002, 67:247-256.

Thomas G., "Medicinal Chemistry: An Introduction," John Wiley & Sons, Ltd., 2000, 12, 17, 243 and 364-372.

Toh H. T. et al., "Studies on vitamin D (calciferol and its analogs. 25. Studies on a convergent route to side-chain analogues . . . ," J. Org. Chem., 1983, 48:1414-1417.

Wermuth C. G., "Designing Prodrugs and Bioprecursors," The Practice of Medicinal Chemistry, 2nd Ed., Academic Press, 2003, 33:561-582.

Arbour, Nancy C. et al., "A Highly Sensitive Method for Large-Scale Measurements of 1,25-Dihydroxyvitamin D," *Analytical Biochemistry*, 1998, vol. 255, pp. 148-154.

Arbour, Nancy C. et al., "TLR4 mutations are associated with endotoxin hyporesponsiveness in humans," *Nature Genetics*, Jun. 2000, vol. 25, pp. 187-191.

International Search Report and Written Opinion of the International Searching Authority for PCT/US2009/031663 dated Mar. 26, 2009.

\* cited by examiner

13,13-DIMETHYL-*DES*-C,D ANALOGS OF 1α,25-DIHYDROXY-19-NOR-VITAMIN D₃ COMPOUNDS AND TOPICAL COMPOSITION DOSAGE FORMS AND METHODS OF TREATING SKIN CONDITIONS THEREOF

CROSS REFERENCE TO RELATED APPLICATIONS

This application claims the benefit of and priority to U.S. Provisional Application No. 61/022,696 filed Jan. 22, 2008, which is incorporated herein by reference in its entirety.

STATEMENT REGARDING GOVERNMENT INTEREST

Not Applicable.

BACKGROUND OF THE INVENTION

The natural hormone, 1α,25-dihydroxyvitamin $D_3$ and its analog in ergosterol series (i.e., 1α,25-dihydroxyvitamin $D_2$) are known to be highly potent regulators of calcium homeostasis in animals and humans. More recently, it has been reported that their activity in cellular differentiation has been established. (Ostrem et al., 1987, *Proc. Natl. Acad. Sci. USA*, 84, 2610). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. Such differences in activity may be useful in the treatment of a variety of diseases such as renal osteodystrophy, vitamin D-resistant rickets, osteoporosis, psoriasis, and certain malignancies.

In 1990, a new class of vitamin D analogs was discovered. The so-called 19-nor-vitamin D compounds were reported, which have been characterized by the replacement of the ring A exocyclic methylene group (carbon 19) (typical of the vitamin D system) by two hydrogen atoms. Biological testing of such 19-nor analogs (e.g., 1α,25-dihydroxy-19-nor-vitamin $D_3$) have revealed a selective activity profile having high potency to induce cellular differentiation with very low calcium mobilizing activity.

Thus, these 19-nor analog compounds have been potentially useful as therapeutic agents for the treatment of malignancies and/or various skin disorders. Two different methods of synthesis of such 19-nor-vitamin D analogs have been reported. (Perlman et al., 1990, *Tetrahedron Letters* 31, 1823); Perlman et al., 1991, *Tetrahedron Letters* 32, 7663); and, U.S. Pat. No. 5,086,191 to DeLuca et al.). A few years later, synthesis of analogs of 1α,25-dihydroxy-19-norvitamin $D_3$ substituted at 2-position with hydroxy or alkoxy groups were reported. (U.S. Pat. No. 5,536,713 to DeLuca et al.) These 19-nor-vitamin D compounds also exhibit interesting and selective activity profiles. Binding sites in vitamin D receptors can accommodate different substituents at C-2 in the synthesized vitamin D analogs.

Recent synthesis and testing of the 19-nor class of pharmacologically important vitamin D compounds has been reported, whereby the analogs are characterized by the transposition of the ring A exocyclic methylene group from carbon 10 (C-10) to carbon 2 (C-2) (i.e., 2-methylene-19-nor-vitamin D compounds have been recently synthesized and tested). (Sicinski et al., 1998, *J. Med. Chem.*, 41, 4662; Sicinski et al., 2002, *Steroids* 67, 247; and, U.S. Pat. Nos. 5,843,928, 5,936,133 and 6,392,071, each to DeLuca et al.). Molecular mechanics studies, performed on these analogs, showed that a change of A-ring conformation can be expected resulting in the "flattening" of the cyclohexanediol ring. From molecular mechanics calculations and NMR studies their A-ring conformational equilibrium was established to be ca. 6:4 in favor of the conformer that has an equatorial 1α-OH. Introduction of the 2-methylene group into 19-nor-vitamin D carbon skeleton changes the character of its (1α- and 3β-) A-ring hydroxyls. They are both now in the allylic positions, similar to the 1α-hydroxyl group (crucial for biological activity) in the molecule of the natural hormone, 1α,25-$(OH)_2D_3$. It was found that 1α,25-dihydroxy-2-methylene-19-norvitamin D analogs are characterized by significant biological potency, enhanced dramatically in compounds with "unnatural" (20S)-configuration.

An interesting modification of the vitamin D skeleton is removal of its C and D rings. The first compound (retiferol) lacking the C,D-substructure, was obtained thirteen years ago (Kutner et al., 1995, *Bioorg. Chem.* 23, 22). Later, several des-C,D vitamin $D_3$ derivatives, including 19-nor analogs, were synthesized. (Bauer et al., U.S. Pat. No. 5,969,190; and, Barbier et al., U.S. Pat. No. 6,184,422) and some compounds (Ro 65-2299) showed improved biological activities. (Hilpert et al., 2001, *Tetrahedron* 57, 681).

Recently, biological testing and synthesis of des-C,D analog of 2-methylene-1α,25-dihydroxy-19-norvitamin $D_3$ have been reported. (DeLuca et al., U.S. Pat. Appl. Publ. No. US 2007/0112077). The analog retained some VDR binding ability and transcriptional activity albeit significantly decreased in comparison to the analogous vitamins possessing intact C,D rings.

SUMMARY OF THE INVENTION

One aspect of the invention is an active pharmaceutical ingredient according to the structure

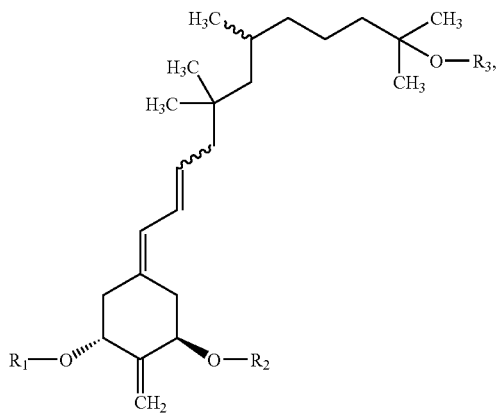

a prodrug thereof, or a solute thereof, wherein $R_1$ is hydrogen or a protecting group, wherein $R_2$ is a hydrogen or a protecting group, wherein $R_3$ is hydrogen or a protecting group, and, wherein each ⁓ is independently ⁓ or ⁓.

In an exemplary embodiment of the active pharmaceutical ingredient, $R_1$, $R_2$ and $R_3$ are each t-butyldimethylsilyl.

In another exemplary embodiment of the active pharmaceutical ingredient, $R_1$, $R_2$ and $R_3$ are each hydrogen.

In another exemplary embodiment of the active pharmaceutical ingredient, the active pharmaceutical ingredient is (1R,3R)-5-[(E)-(S)-11'-hydroxy-5',5',7',11'-tetramethyl-dodec-2'-enylidene]-2-methylene-cyclohexane-1,3-diol and/ or (1R,3R)-5-[(Z)-(S)-11'-hydroxy-5',5',7',11'-tetramethyl-dodec-2'-enylidene]-2-methylene-cyclohexane-1,3-diol.

In another exemplary embodiment of the active pharmaceutical ingredient, the active pharmaceutical ingredient is (1R,3R)-5-[(E)-(R)-11'-hydroxy-5',5',7',11'-tetramethyl-dodec-2'-enylidene]-2-methylene-cyclohexane-1,3-diol and/or (1R,3R)-5-[(Z)-(R)-11'-hydroxy-5',5',7',11'-tetramethyl-dodec-2'-enylidene]-2-methylene-cyclohexane-1,3-diol.

Another aspect of the invention is a method of making a diastereomeric mixture of a protected active pharmaceutical ingredient comprising the steps or acts of providing a racemic mixture of an aldehyde reactant according to the structure

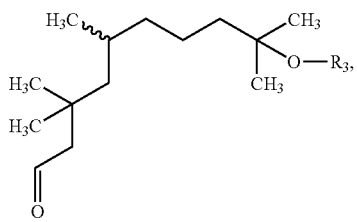

and, reacting the aldehyde reactant with an allylic phosphine oxide reactant according to the structure

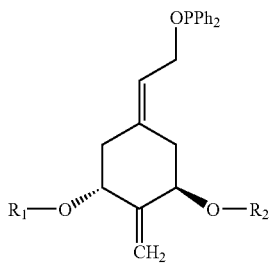

to yield a diastereomeric mixture of a protected active pharmaceutical ingredient according to the structure

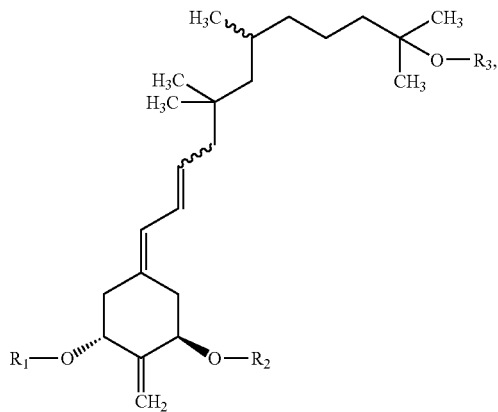

wherein $R_1$, $R_2$ and $R_3$ are each a protecting group, and, wherein each ⁓ is independently ⁓ or ▰. Diastereomers are stereoisomers that differ at some stereocenters but not at others, so they are not mirror images (enantiomers).

In an exemplary embodiment of the method of making a diastereomeric mixture of an active pharmaceutical ingredient, $R_1$, $R_2$ and $R_3$ are each t-butyldimethylsilyl.

In another exemplary embodiment of the method of making a diastereomeric mixture of an active pharmaceutical ingredient, the method further comprises the steps or acts of separating and deprotecting the protected active pharmaceutical ingredient to yield a deprotected active pharmaceutical ingredient according to the structure

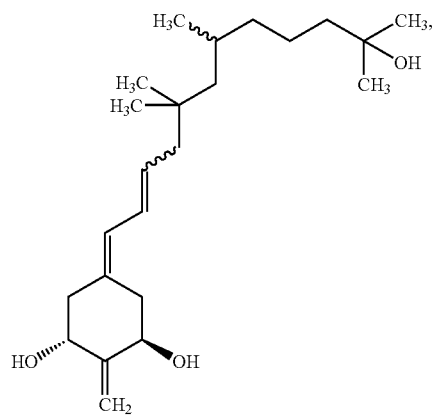

wherein the deprotecting and separating are performed in either sequence.

In another exemplary embodiment of the method of making a diastereomeric mixture of an active pharmaceutical ingredient, the diastereomeric mixture of the deprotected active pharmaceutical ingredient comprises (1R,3R)-5-[(E)-(S)-11'-hydroxy-5',5',7',11'-tetramethyl-dodec-2'-enylidene]-2-methylene-cyclohexane-1,3-diol and (1R,3R)-5-[(Z)-(S)-11'-hydroxy-5',5',7',11'-tetramethyl-dodec-2'-enylidene]-2-methylene-cyclohexane-1,3-diol.

In another exemplary embodiment of the method of making a diastereomeric mixture of an active pharmaceutical ingredient, the diastereomeric mixture of the deprotected active pharmaceutical ingredient comprises (1R,3R)-5-[(E)-(R)-11'-hydroxy-5',5',7',11'-tetramethyl-dodec-2'-enylidene]-2-methylene-cyclohexane-1,3-diol and (1R,3R)-5-[(Z)-(R)-11'-hydroxy-5',5',7',11'-tetramethyl-dodec-2'-enylidene]-2-methylene-cyclohexane-1,3-diol.

Another aspect of the invention is a method of making separated diastereomers of an active pharmaceutical ingredient comprising the steps or acts of providing an enantiomer of an aldehyde reactant according to the structure

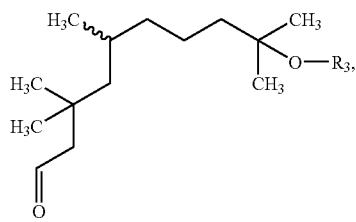

reacting the aldehyde reactant with an allylic phosphine oxide reactant according to the structure

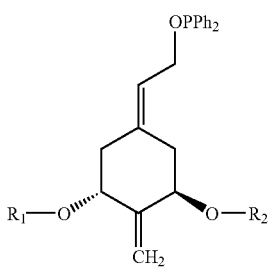

to yield a mixture of geometric isomers of a protected active pharmaceutical ingredient according to the structure

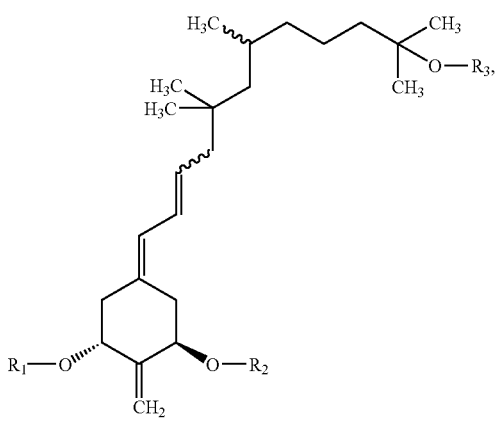

wherein $R_1$, $R_2$ and $R_3$ are each a protecting group, and, wherein each ⁓ is independently ⁓ or ⁓, deprotecting the mixture of geometric isomers of the protected active pharmaceutical ingredient to yield an isomeric mixture of a deprotected active pharmaceutical ingredient according to the structure

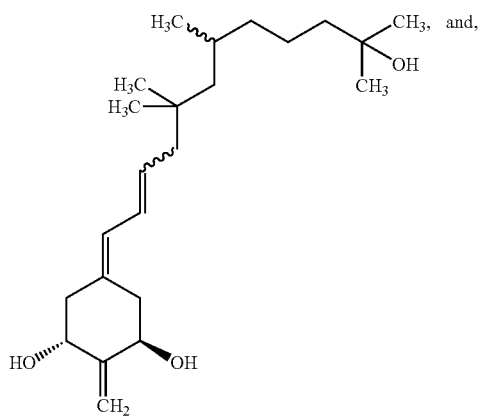

separating the mixture of geometric isomers of the deprotected active pharmaceutical ingredient to yield the separated isomers of the deprotected active pharmaceutical ingredient, wherein the deprotecting and separating acts or steps may be performed in either sequence.

In an exemplary embodiment of the method of making separated geometric isomers of an active pharmaceutical ingredient, $R_1$, $R_2$ and $R_3$ are each t-butyldimethylsilyl.

In another exemplary embodiment of the method of making separated geometric isomers of an active pharmaceutical ingredient, $R_1$, $R_2$ and $R_3$ are each hydrogen.

In another exemplary embodiment of the method of making separated geometric isomers of an active pharmaceutical ingredient, the separated geometric isomers of the deprotected active pharmaceutical ingredient comprise (1R,3R)-5-[(E)-(S)-11'-hydroxy-5',5',7',11'-tetramethyl-dodec-2'-enylidene]-2-methylene-cyclohexane-1,3-diol and (1R,3R)-5-[(Z)-(S)-11'-hydroxy-5',5',7',11'-tetramethyl-dodec-2'-enylidene]-2-methylene-cyclohexane-1,3-diol.

In another exemplary embodiment of the method of making separated geometric isomers of an active pharmaceutical ingredient, the separated geometric isomers of deprotected active pharmaceutical ingredient comprise (1R,3R)-5-[(E)-(R)-11'-hydroxy-5',5',7',11'-tetramethyl-dodec-2'-enylidene]-2-methylene-cyclohexane-1,3-diol and (1R,3R)-5-[(Z)-(R)-11'-hydroxy-5',5',7',11'-tetramethyl-dodec-2'-enylidene]-2-methylene-cyclohexane-1,3-diol.

Another aspect of the invention is an active pharmaceutical ingredient made by any one of the above methods.

Another aspect of the invention is a topical dosage form composition comprising a therapeutically effective dose of any one of the above active pharmaceutical ingredients and a pharmaceutically suitable topical carrier system.

In an exemplary embodiment of the topical composition, the dose is in the range of 36 mg to 11 ng/kg$_{BW}$/day.

In another exemplary embodiment of the topical composition, the topical carrier system comprises in the range of 30-70% ethanol and 30-70% propylene glycol.

In an exemplary embodiment of the topical composition, the topical carrier system comprises 70% ethanol and 30% propylene glycol.

Another aspect of the invention is a method of treating acne comprising the steps or acts of topically administering daily or intermittently any one of the above topical compositions to a human.

Another aspect of the invention is a method of reducing comedone area comprising the steps or acts of topically administering daily or intermittently any one of the above topical compositions to a human.

Another aspect of the invention is a method of treating psoriasis comprising the steps or acts of topically administering daily or intermittently any one of the above topical compositions to a human.

Another aspect of the invention is a method of treating ichthyosis comprising the steps or acts of topically administering daily or intermittently any one of the above topical compositions to a human.

Another aspect of the invention is a method of treating photoaging or photodamaged skin comprising the steps or acts of topically administering daily or intermittently any one of the above topical compositions to a human.

Another aspect of the invention is a method of treating skin cancer comprising the steps or acts of topically administering daily or intermittently any one of the above topical compositions of to a human.

Another aspect of the invention is a topical dosage form composition comprising a therapeutically effective dose of an active pharmaceutical ingredient according to the formula

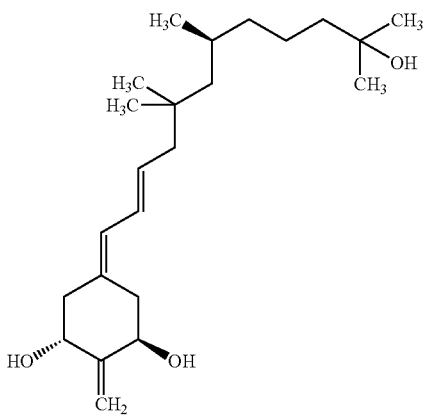

(13,13-dimethyl-des-C,D analog of (20S)-2-methylene-1α, 25-dihydroxy-19-nor-vitamin $D_3$ that is also referred to as 13Me$_2$ herein)(molecular weight=364.57), or a solute thereof, and, a pharmaceutically suitable topical carrier system.

In an exemplary embodiment of the composition, the dose is in the range of 36 mg to 11 ng/kg$_{BW}$/day.

In another exemplary embodiment of the composition, the topical carrier system comprises 70% ethanol and 30% propylene glycol.

In another exemplary embodiment of the composition, the topical carrier system comprises 70% ethanol and 30% propylene glycol.

Another aspect of the invention is a method of treating acne comprising the acts or steps of topically administering daily or intermittently any one of the above compositions to a human.

Another aspect of the invention is a method of reducing comedone area comprising the acts or steps of topically administering daily or intermittently any one of the above compositions to a human.

Another aspect of the invention is a method of treating psoriasis comprising the acts or steps of topically administering daily or intermittently any one of the above compositions to a human.

Another aspect of the invention is a method of treating ichthyosis comprising the acts or steps of topically administering daily or intermittently any one of the above compositions to a human.

Another aspect of the invention is a method of treating photoaging or photodamaged skin comprising the acts or steps of topically administering daily or intermittently any one of the above compositions to a human.

Another aspect of the invention is a method of treating skin cancer comprising the acts or steps of topically administering daily or intermittently any one of the above compositions to a human.

BRIEF DESCRIPTION OF DRAWINGS OF THE EXEMPLARY EMBODIMENTS

Figure 1:
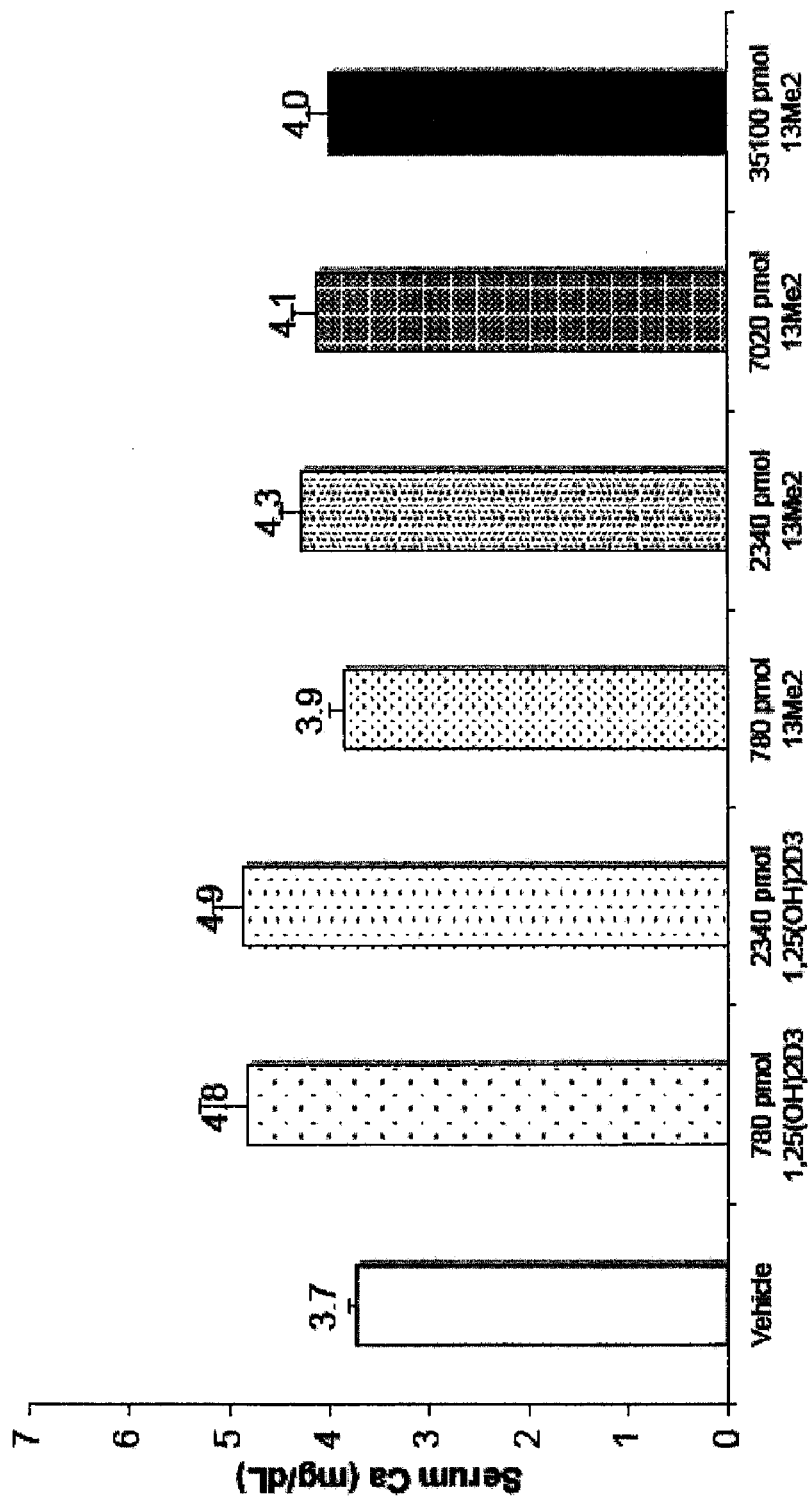
FIG. 1 is a graph showing bone calcium mobilization in rats for 13Me$_2$ and 1.25(OH)$_2$D$_3$.
Figure 2:
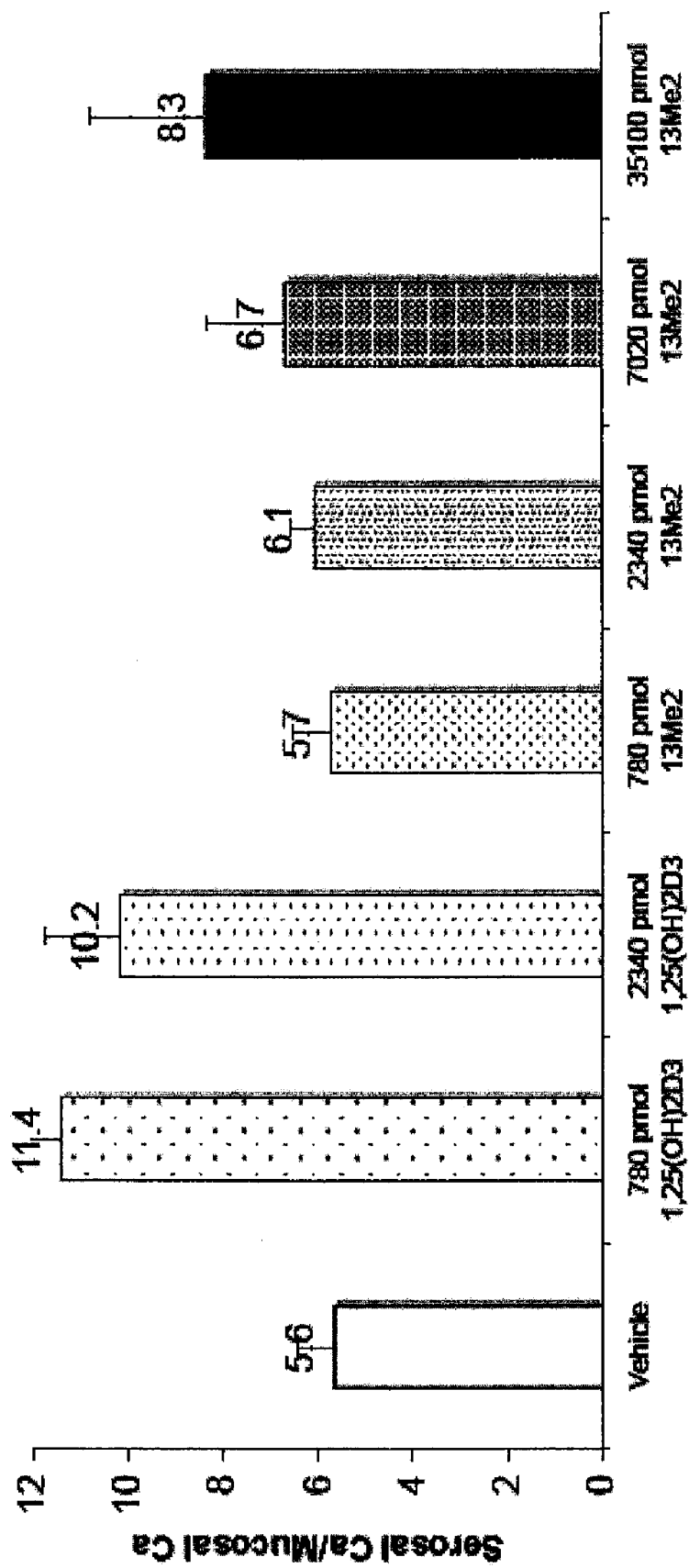
FIG. 2 is a graph showing intestinal calcium transport in rats for 13Me$_2$ and 1.25(OH)$_2$D$_3$.
Figure 3:
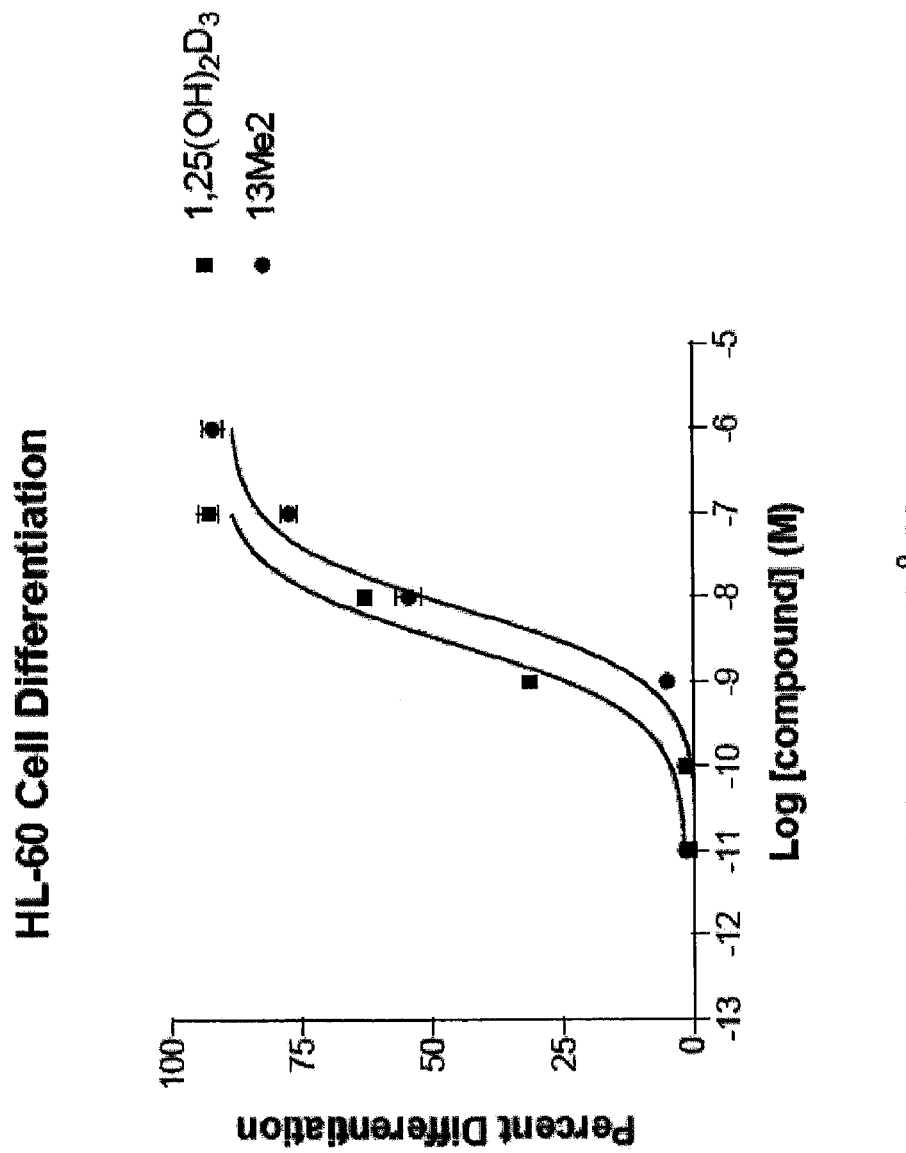
FIG. 3 is a graph showing HL-60 cell differentiation for 13Me$_2$ and 1.25(OH)$_2$D$_3$ causing the differentiation of HL-60 cells into monocytes.
Figure 4:
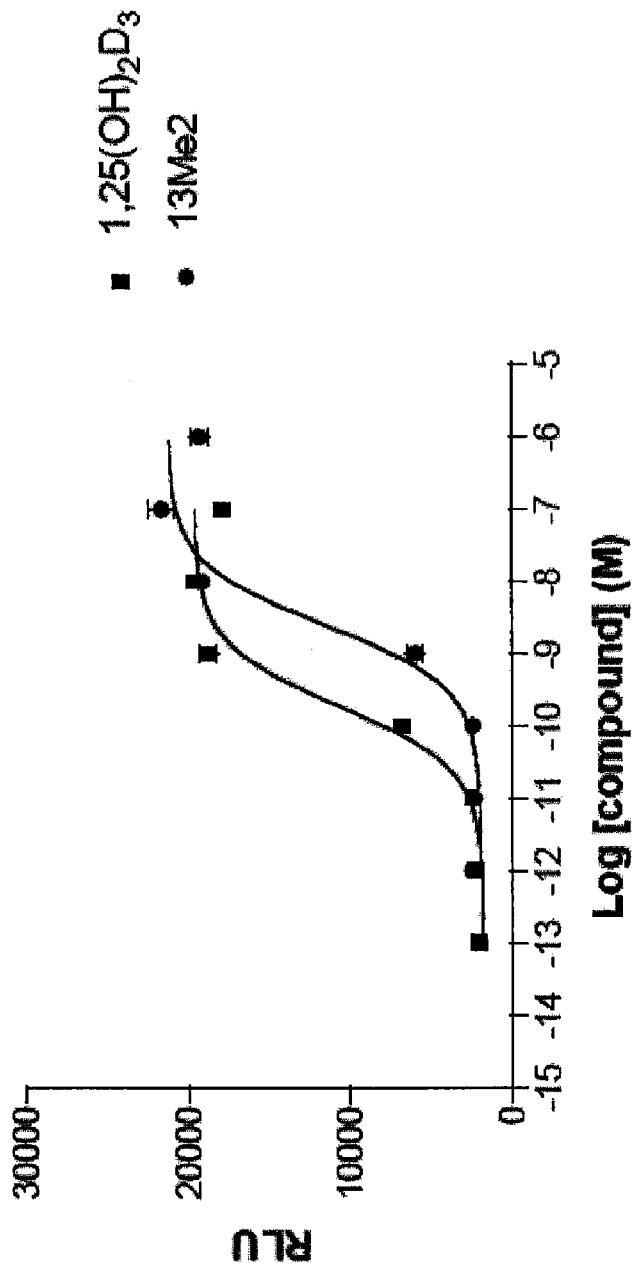
FIG. 4 is a graph showing in vitro 24-OHase transcription for 13Me$_2$ and 1.25(OH)$_2$D$_3$.
Figure 5:
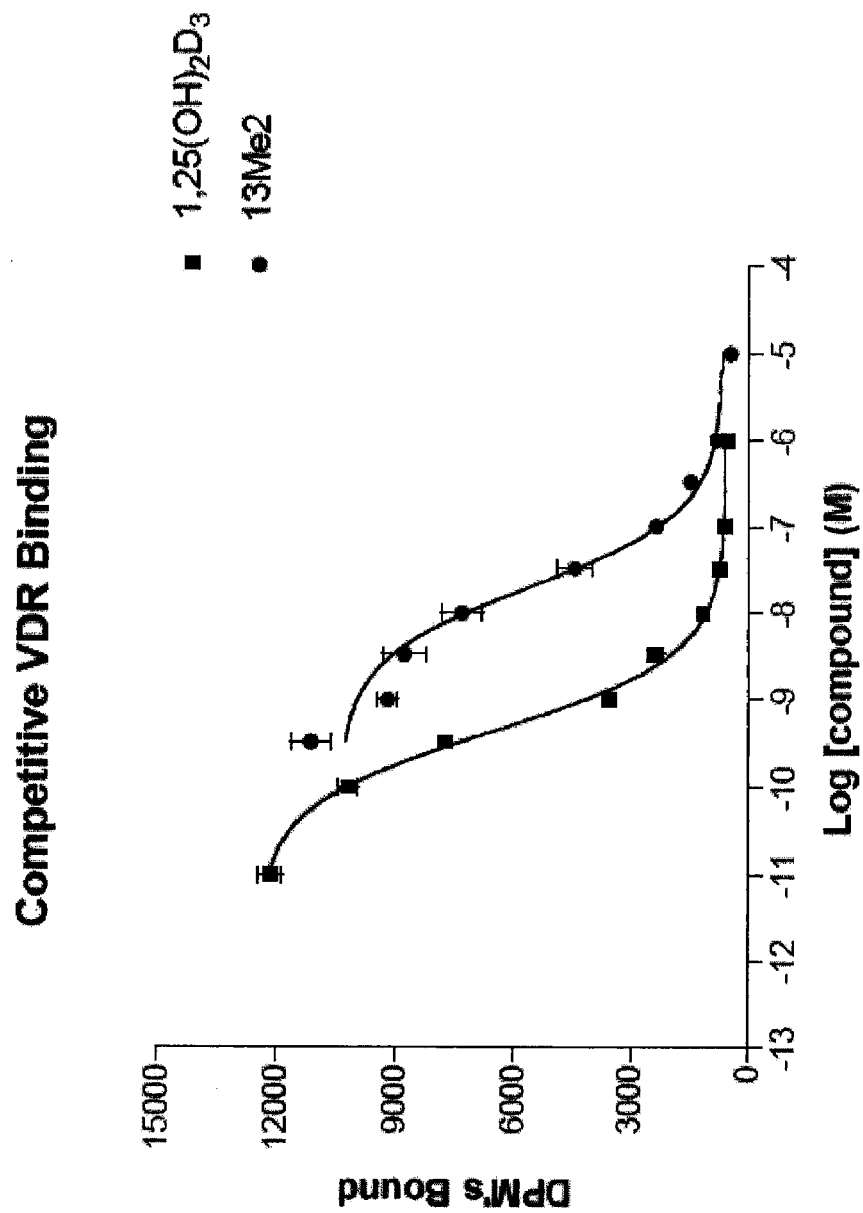
FIG. 5 is a graph showing competitive VDR binding to the nuclear hormone receptor for 13Me$_2$ and 1.25(OH)$_2$D$_3$.
Figure 6:
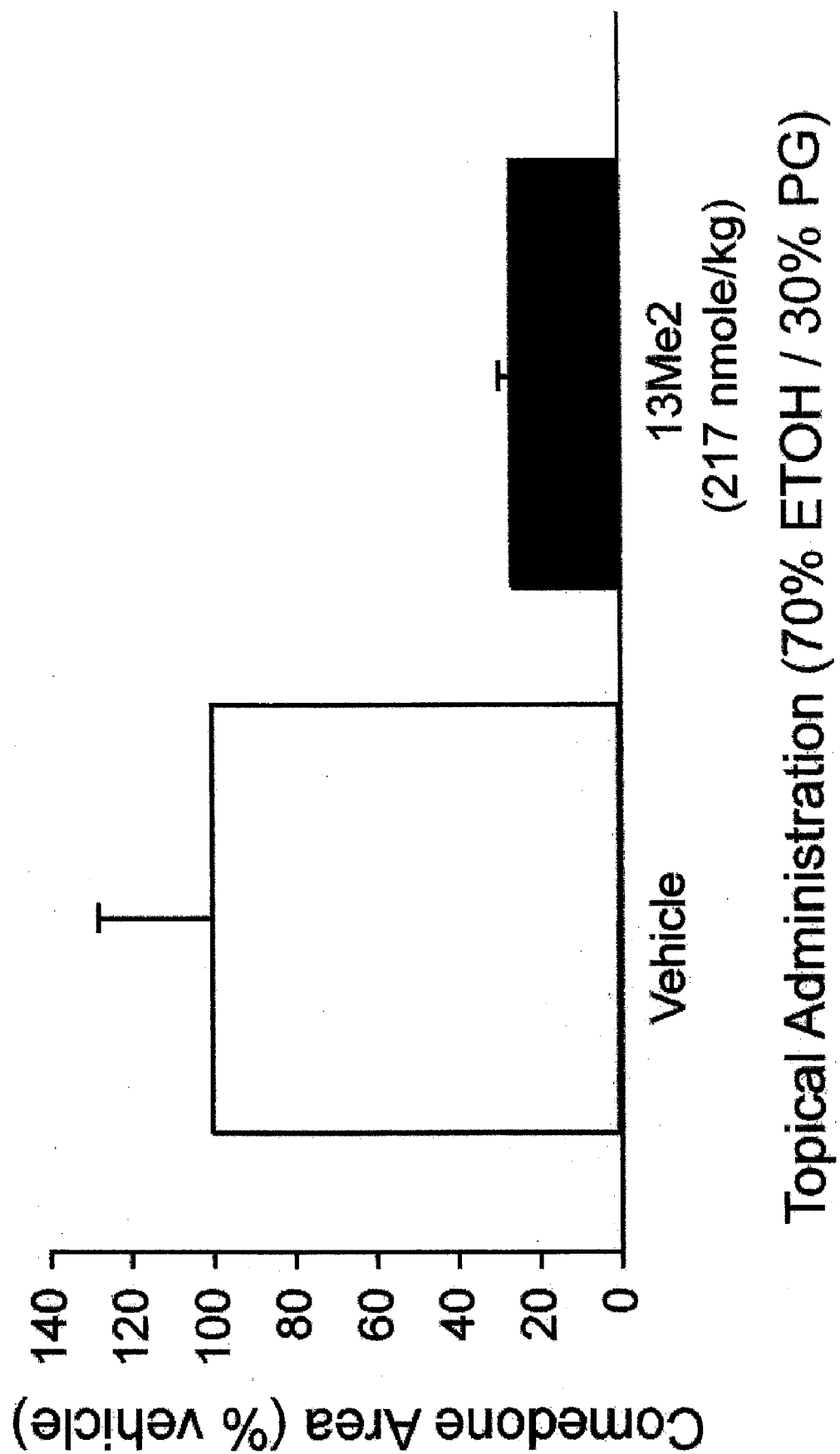

FIG. 6 is a bar graph showing comedone area for Rhino mice treated topically with 13Me$_2$ alone at a dose of 217 nmole/kg$_{BW}$/day compared to Rhino mice treated topically with the carrier vehicle alone, whereby the API was formulated in a carrier vehicle comprising 70 vol % ethanol and 30 vol % propylene glycol, whereby comedone area was analyzed after 3 weeks of daily topical treatment, and whereby 13Me$_2$ produced a significant reduction in comedone area relative to the vehicle-treated group.

Figure 7:
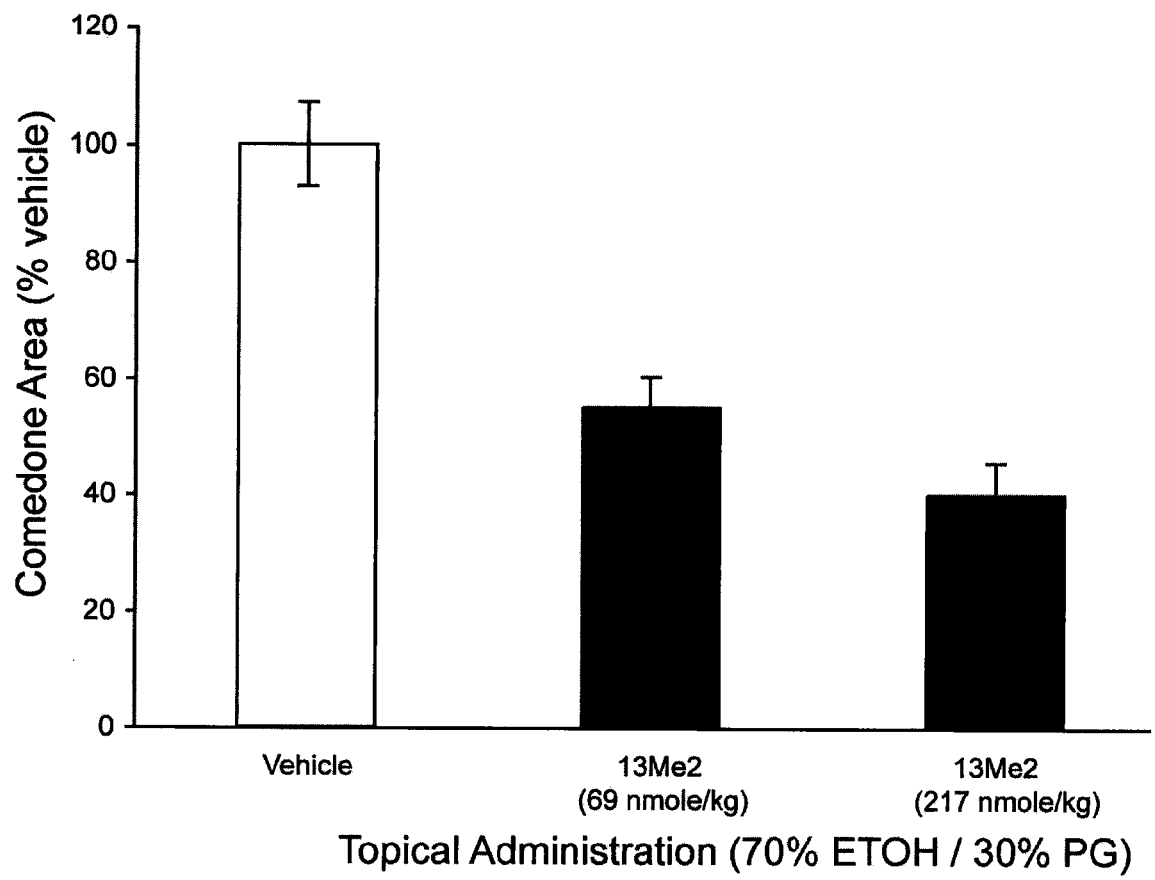

FIG. 7 is a bar graph showing comedone area for Rhino mice treated topically with 13Me$_2$ alone at doses of 69 and 217 nmole/kg$_{BW}$/day compared to Rhino mice treated topically with the carrier vehicle alone, whereby the API was formulated in a carrier vehicle comprising 70% vol % ethanol and 30% vol % propylene glycol, whereby comedone area was analyzed after 3 weeks of daily topical treatment, and whereby 13Me$_2$ produced a dose-dependent reduction in comedone area relative to the vehicle-treated group.

DETAILED DESCRIPTION OF THE EXEMPLARY EMBODIMENTS

The invention is directed to 13,13-dimethyl-des-C,D analogs of 1α,25-dihydroxy-19-nor-vitamin $D_3$ compounds and topical composition dosage forms thereof, and methods of treating skin conditions thereof. Exemplary active pharmaceutical ingredients include (1R,3R)-5-[(E)-(S)-11'-hydroxy-5',5',7',11'-tetramethyl-dodec-2'-enylidene]-2-methylene-cyclohexane-1,3-diol, (1R,3R)-5-[(Z)-(S)-11'-hydroxy-5',5',7',11'-tetramethyl-dodec-2'-enylidene]-2-methylene-cyclohexane-1,3-diol, (1R,3R)-5-[(E)-(R)-11'-hydroxy-5',5',7',11'-tetramethyl-dodec-2'-enylidene]-2-methylene-cyclohexane-1,3-diol, and (1R,3R)-5-[(Z)-(R)-11'-hydroxy-5',5',7',11'-tetramethyl-dodec-2'-enylidene]-2-methylene-cyclohexane-1,3-diol.

A class of 1α,25-dihydroxylated 19-nor-vitamin $D_3$ compounds not known heretofore are the 2-methylene compounds lacking the C,D-rings and having two methyl groups attached to C-13. Thus, taking into account a carbon skeleton of these compounds, they can be formally considered as derivatives of 8(12),14(17)-diseco-9,11,15,16,19-pentanor-vitamin $D_3$. The preferred vitamin D analog is 13,13-dimethyl-2-methylene-1α,25-dihydroxy-des-C,D-19-nor-vitamin $D_3$.

The invention is also directed to preparation of des-C,D vitamins substituted with groups (such as alkyls) having increased hydrophobic interaction with VDR binding. Biologically active 2-methylene-19-norvitamin D compounds, and analogs thereof characterized by the absence of the C,D-rings in lieu of two methyl groups at C-13 have been synthesized and tested.

Structurally these novel analogs are characterized by the general formula I shown below:

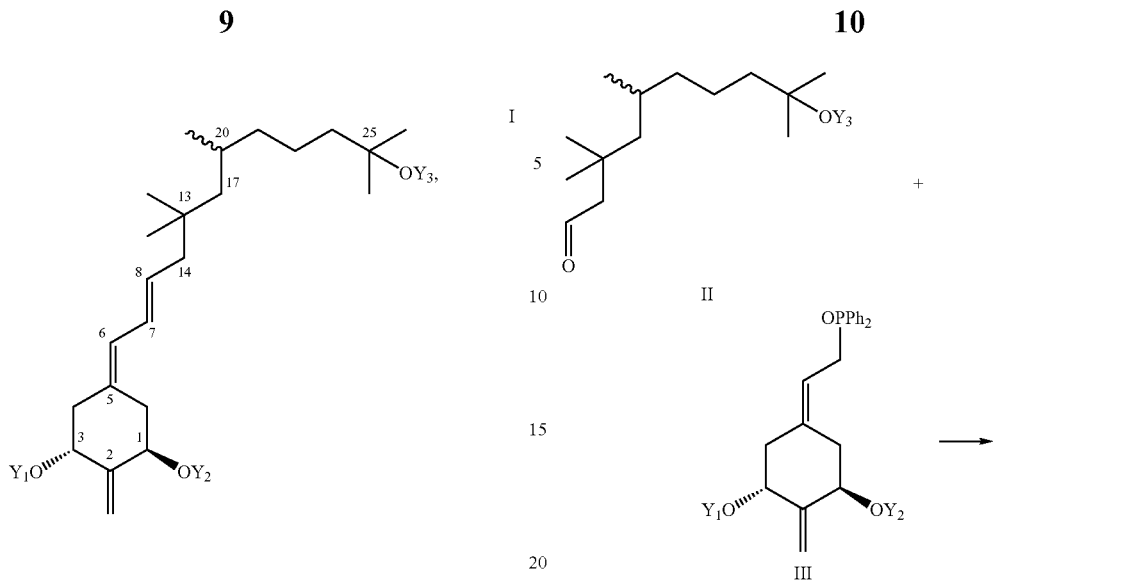

wherein $Y_1$ and $Y_2$, which may be the same or different, are each hydrogen or a hydroxy-protecting group. Notably, as used herein, $Y_1=R_1$; $Y_2=R_2$; and $Y_3=R_3$. An exemplary analog is 13,13-dimethyl-2-methylene-1α,25-dihydroxy-des-C,D-19-nor-vitamin $D_3$ which has the following formula Ia:

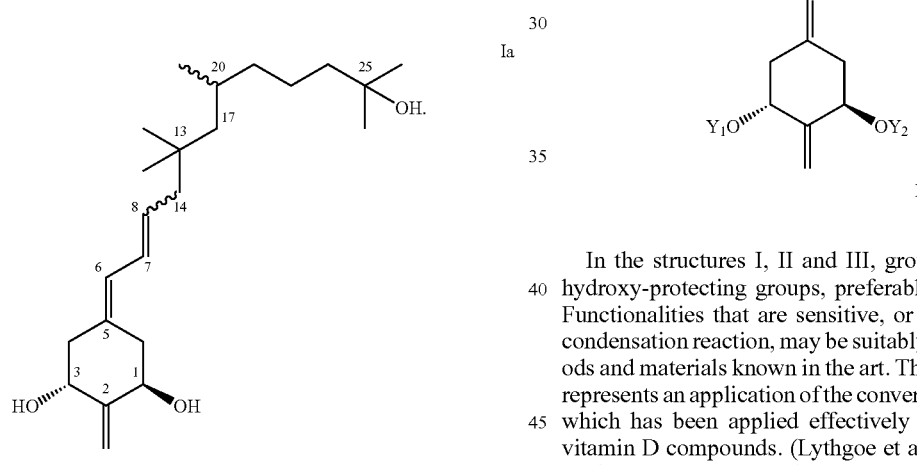

In the general formula I, the chiral carbon 20 may be in either the R or S configuration, whereby the wavy line to the carbon 14 (steroidal numbering) indicates that the double bond between carbons 7 and 8 may be in either the E or Z configuration.

The phrase "hydroxy-protecting group" refers to any suitable group, such as tert-butyloxy-carbonyl (t-BOC) and t-butyl-dimethyl-silyl (TBS). Other hydroxy protecting groups are shown in Greene T W et al., 1999, *Protective Groups in Organic Synthesis*, John Wiley & Sons, Inc., pp. 17-200, which is incorporated herein by reference in its entirety.

Preparation of the vitamin $D_3$ analogs having the structure I is performed using a Wittig-Horner coupling of the aldehyde II with the allylic phosphine oxide III to the corresponding 13,13-dimethyl-2-methylene-1α,25-dihydroxy-des-C,D-19-nor-vitamin $D_3$ derivative I followed by deprotection of hydroxyls at C-1, C-3 and C-25 in the latter compound:

In the structures I, II and III, groups $Y_1$, $Y_2$ and $Y_3$ are hydroxy-protecting groups, preferably t-butyldimethylsilyl. Functionalities that are sensitive, or that interfere with the condensation reaction, may be suitably protected using methods and materials known in the art. The process shown above represents an application of the convergent synthesis concept, which has been applied effectively for the preparation of vitamin D compounds. (Lythgoe et al., 1978, *J. Chem. Soc. Perkin Trans. I,* 590; Lythgoe, 1983, *Chem. Soc. Rev.* 9, 449; Toh et al., 1983, *J. Org. Chem.* 48, 1414; Baggiolini et al., 1986, *J. Org. Chem.* 51, 3098; Sardina et al., 1986, *J. Org. Chem.* 51, 1264 and *J. Org. Chem.* 51, 1269(1986); DeLuca et al., U.S. Pat. No. 5,086,191; and, DeLuca et al., U.S. Pat. No. 5,536,713).

Preparation of the required aldehyde of the structure II. A new synthetic route has been developed starting from the known (S)-7-benzyloxymethoxy-2,6-dimethyl-heptan-2-ol (DeLuca et al., U.S. Pat. Appl. Publ. No. US 2007/0112077). A process involving transformation of the starting alcohol 2, prepared in 6 steps from commercially available (1R,3R,4S,5R)-(−)-quinic acid, into the aldehyde 14, and its subsequent coupling with the phosphine oxide 15, is summarized by the Scheme I and Scheme II.

Thus, the tertiary hydroxy group in 2 was protected as TBS ether and primary hydroxyl was deprotected by hydrogenation of the formed ether 3. Oxidation of the alcohol 4 provided the aldehyde 5 which was subjected to Still-Gennari reaction with the phosphono ester 6. The resulted mixture of the isomeric unsaturated esters 7 was hydrogenated to the saturated compounds 8. Alkylation process of the carbanions (generated from these esters by LDA) resulted in the introduction of a methyl substituent in the α position to the carbomethoxy group.

DIBALH reduction of the formed methylated esters 9 provided the alcohols 10 which were converted to imidazole-1-carbothioic acid esters 11. These, in turn, were subjected to reduction with tributyltin hydride to yield the expected compound 12 possessing gem-dimethyl group. Deprotection of primary hydroxy group in 12 gave the alcohol 13 which was oxidized to the aldehyde 14. Wittig-Horner coupling of this compound with lithium phosphinoxy carbanion (generated from the phosphine oxide 15 and phenyllithium) yielded the expected mixture of protected vitamin D analogs. After deprotection with hydrogen fluoride, 13,13-dimethyl-des-C,D analogs of (20S)-2-methylene-1α,25-dihydroxy-19-nor-vitamin $D_3$ (16 and 17) were produced.

For the preparation of the required phosphine oxides of general structure III, a synthetic route has been developed starting from a methyl quinicate derivative which is easily obtained from commercial (1R,3R,4S,5R)-(−)-quinic acid as described in Sicinski et al., 1998, *J. Med. Chem.* 41, 4662 and U.S. Pat. No. 5,843,928 to DeLuca et al.

SCHEMES I and II set forth herein below in the examples show a detailed illustration of the preparation of compounds of formula Ia, and specifically 13,13-dimethyl-des-C,D analogs of (20S)-2-methylene-1α,25-dihydroxy-19-nor-vitamin $D_3$.

As used herein, "therapeutically effective dose" and "administering to a human a therapeutically effective dose" refers to an amount of one or more APIs sufficient to treat (e.g., prophylactic, treating the active condition or curing) one or more of acne vulgaris, psoriasis, ichthyosis, photoaging, photodamaged skin, and/or skin cancer.

Treatment regimens may also include numerous dosing regimens. For a human, various therapeutically effective doses and dosing regimens thereof may be determined from the animal data set forth herein using known Allometric Scaling (AS) factors. For example, for a mouse having a body weight of 0.03 kg, the AS factor is around 7 assuming a human body weight of 70 kg.

The predictive dosing range set forth in Table 2 was calculated assuming that the dose given to the Rhino mouse has been corrected for the expected lesser sensitivity of the human and further increased by 0.5 log dose. For the high end of the topical dose, the value was further multiplied by a factor of 20 as humans absorb only about 5% of the dose compared to 100% by the mouse. The low dose is $1 \times 10^6$ lower than the high dose. Differences in the animal species sensitivity to various vitamin D analogs as well as differences in relative absorption of various vitamin D analogs by the skin may also significantly affect the human efficacious dose compared to that used in the animal studies detailed herein.

The pharmaceutically suitable topical carrier system (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect.

As used herein, the topical dosage form includes various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles), ointments (a semisolid dosage form, usually containing <20% water and volatiles 5 and >50% hydrocarbons, waxes, or polyols as the vehicle, whereby this dosage form is generally for external application to the skin or mucous membranes), ointment augmented (an ointment dosage form that enhances drug delivery, whereby augmentation does not refer to the strength of the drug in the dosage form), creams (an emulsion, semisolid dosage form, usually containing >20% water and volatiles 5 and/or <50% hydrocarbons, waxes, or polyols as the vehicle, whereby this dosage form is generally for external application to the skin or mucous membranes), cream augmented (a cream dosage form that enhances drug delivery, whereby augmentation does not refer to the strength of the drug in the dosage form), emulsion (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release (a liquid preparation consisting of solid particles dispersed throughout a liquid phase in which the particles are not soluble; the suspension has been formulated in a manner to allow at least a reduction in dosing frequency as compared to that drug presented as a conventional dosage form, e.g., as a solution or a prompt drug-releasing, conventional solid dosage form), pastes (A semisolid dosage form, containing a large proportion, 20-50%, of solids finely dispersed in a fatty vehicle, whereby this dosage form is generally for external application to the skin or mucous membranes), solutions (a clear, homogeneous liquid 1 dosage form that contains one or more chemical substances dissolved in a solvent or mixture of mutually miscible solvents), powders, shampoos (a lotion dosage form which has a soap or detergent that is usually used to clean the hair and scalp; it is often used as a vehicle for dermatologic agents), shampoo suspensions (a liquid soap or detergent containing one or more solid, insoluble substances dispersed in a liquid vehicle that is used to clean the hair and scalp and is often used as a vehicle for dermatologic agents), aerosol foams (i.e., a dosage form containing one or more active ingredients, surfactants, aqueous or nonaqueous liquids, and the propellants; if the propellant is in the internal discontinuous phase, i.e., of the oil-in-water type, a stable foam is discharged, and if the propellant is in the external continuous phase, i.e., of the water-in-oil type, a spray or a quick-breaking foam is discharged), sprays (a liquid minutely divided as by a jet of air or steam), metered spray (a non-pressurized dosage form consisting of valves which allow the dispensing of a specified quantity of spray upon each activation), suspension spray (a liquid preparation containing solid particles dispersed in a liquid vehicle and in the form of coarse droplets or as finely divided solids to be applied locally, most usually to the nasalpharyngeal tract, or topically to the skin), jellies (a class of gels, which are semisolid systems that consist of suspensions made up of either small inorganic particles or large organic molecules interpenetrated by a liquid—in which the structural coherent matrix contains a high portion of liquid, usually water), films (a thin layer or coating), film extended release (a drug delivery system in the form of a film that releases the drug over an extended period in such a way as to maintain constant drug levels in the blood or target tissue), film soluble (a thin layer or coating which is susceptible to being dissolved when in contact with a liquid), sponges (a porous, interlacing, absorbent material that contains a drug, whereby it is typically used for applying or introducing medication, or for cleansing, and whereby a sponge usually retains its shape), swabs (a small piece of relatively flat absorbent material that contains a drug, whereby a swab may also be attached to one end of a small stick, and whereby a swab is typically used for applying medication or for cleansing), patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, "prodrugs" are compounds that are pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzyme controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism. For example, the first prodrug, antibacterial prontosil, is metabolized in vivo to its active metabolite sulphanilamide. Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as a bipartate prodrug. Prodrugs where the carrier is linked to the drug by a separate structure are referred to as tripartate prodrugs, whereby the carrier is removed by an enzyme-controlled metabolic process, and whereby the linking structure is removed by an enzyme system or by a chemical reaction. (Thomas G, *Medicinal Chemistry: An Introduction,* 2000, John Wiley & Sons, Ltd. pp. 12, 17, 243 and 364-372)(See also, Wermuth C G, 2003, *The Practice of Medicinal Chemistry, 2nd Ed.*, Academic Press 33:561-582).

EXAMPLES

Chemistry. Melting points (uncorrected) were determined on a Thomas-Hoover capillary melting-point apparatus. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 200, 400 and 500 MHz with a Varian Unity, Bruker DMX-400 and Bruker DMX-500 spectrometers, respectively. $^{13}$C nuclear magnetic resonance (NMR) spectra were recorded at 50, 100 and 125 MHz with the same spectrometers in deuteriochloroform. Chemical shifts ($\delta$) were reported downfield from internal $Me_4Si$ ($\delta$ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

The starting (S)-7-benzyloxymethoxy-2,6-dimethyl-heptan-2-ol (2) was obtained from commercial R-(−)-methyl-3-hydroxy-2-methylpropionate as described previously (DeLuca et al., U.S. Pat. Appl. Publ. No. US 2007/0112077).

Example 1

Preparation of 13,13-dimethyl-des-C,D analogs of (20S)-2-methylene-1α,25-dihydroxy-19-nor-vitamin $D_3$ 16 (13Me$_2$) and 17 (13Me$_2$-C)

(a) Protection of hydroxy group in the hydroxy ether 2 (SCHEME I). [(S)-6-Benzyloxymetoxy-1,1,5-trimetyl-hexyloxy]-tert-butyldimethylsilane (3). To a solution of alcohol 2 (1.08 g, 3.9 mmol) and 2,6-lutidine (0.9 mL, 7.7 mmol) in anhydrous $CH_2Cl_2$ (21 mL) at 0° C. was dropwise added tert-butyldimethylsil-triflate (1.46 mL, 6.1 mmol). The solution was stirred at 0° C. for 1.5 h and poured into water. The organic layer was separated, and the water phase was extracted with $CH_2Cl_2$. The combined extracts were washed with diluted HCl, dried ($MgSO_4$) and evaporated. The oily residue was chromatographed on silica gel using hexane/AcOEt (9:1) as an eluent to provide the oily product 3 (1.4 g, 100%).

3: $[\alpha]^{24}_D$ −4° (c 0.19, $CHCl_3$); $^1H$ NMR (200 MHz, $CDCl_3$) δ 0.06 [6H, s $Si(CH_3)_2$], 0.85 (9H, s, Si-t-Bu), 0.94 (3H, d, J=6.6 Hz, CH—$CH_3$), 1.17 [6H, s, $C(CH_3)_2$], 1.74 (1H, m, CH—$CH_3$), 3.36 (1H, dd, J=9.3, 6.6 Hz, one of $OCH_2$—CH), 3.46 (1H, dd, J=9.3, 6.1 Hz, one of $OCH_2CH$), 4.60 (2H, s, O—$CH_2$—O), 4.76 (2H, s, $CH_2$-Ph), 7.30 (5H, m, Ar—H); $^{13}C$ NMR (50 MHz) δ −1.84 [$Si(CH_3)_2$], 17.31 (CH—$CH_3$), 18.31 [$SiC(CH_3)_3$], 21.80 ($CH_2CH_2CH_2$), 26.05 [$SiC(CH_3)_3$], 29.96 and 30.09 [$C(CH_3)_2$], 33.69 (CH—$CH_3$), 34.36 ($CH_2CH_2CH_2$), 45.49 ($CH_2CH_2CH_2$), 69.43 ($CH_2$-Ph), 73.66 [$C(CH_3)_2$], 73.84 ($OCH_2CH$), 94.98 ($OCH_2O$), 127.86, 128.11 and 128.62 ($Ar_{orto,meta,para}$), 138.21 ($Ar_{ipso}$); HRMS (ESI) exact mass calcd for $C_{23}H_{42}O_3SiNa$ ($M^+$+Na) 417.2801, measured 417.2805.

(b) Removal of BOM-protecting group in compound 3. (s)-6-(tert-Butyldimethylsilyloxy)-2,6-dimethyl-heptan-1-ol (4). $1^{st}$ procedure. To a solution of compound 3 (1.5 g, 3.8 mmol) in ethyl acetate (10 mL) was added Pd/C (10%, 100 mg) at room temperature. The reaction mixture was stirred for 6 days under a continuous stream of hydrogen (from balloon) and Pd/C (100 mg in portions) was added 3 times per day. Then, the mixture was filtered and the solvent was evaporated under reduced pressure. The oily residue was chromatographed on silica gel using hexane/AcOEt (9:1) as an eluent yielding an oily alcohol 4 (0.80 g, 77%).

$2^{nd}$ procedure. To a solution of compound 3 (0.5 g, 1.27 mmol) in ethyl acetate (25 mL) was added Pd/C (10%, 380 mg) at room temperature. The reaction mixture was hydrogenated for 3 h under the hydrogen pressure of 10 Pa. Then, the mixture was filtered and the solvent was evaporated under reduced pressure. The oily residue was applied on a silica Sep-Pak cartridge (5 g) and washed with hexane/AcOEt (9:1) producing an oily alcohol 4 (272 mg, 78%).

4: $[\alpha]^{24}_D$ −5.3° (c 0.93, $CHCl_3$); $^1H$ NMR (400 MHz, $CDCl_3$) δ 0.06 [6H, s, $Si(CH_3)_2$], 0.85 (9H, s, Si-t-Bu), 1.09 (3H, d, J=7.1 Hz, CH—$CH_3$), 1.17 [6H, s, $C(CH_3)_2$], 1.63 (1H, m, $CH_3CH$), 3.42 (1H, dd, J=6.6, 10.5 Hz, one of $CH_2OH$), 3.51 (1H, dd, J=5.8, 10.5 Hz, one of $CH_2OH$); $^{13}C$ NMR (100 MHz) δ −2.07 [$Si(CH_3)_2$], 16.54 (CH—$CH_3$), 18.09 [$SiC(CH_3)_3$], 21.56 ($CH_2$—$CH_2$—$CH_2$), 25.82 [$SiC(CH_3)_3$], 29.76 and 29.87 [$2\times C(CH_3)_2$], 33.69 ($CH_2CH_2CH_2$), 35.78 (CH—$CH_3$), 45.28 ($CH_2CH_2CH_2$), 68.78 ($CH_2OH$), 73.45 [$C(CH_3)_2$]; HRMS (ESI) exact mass calcd for $C_{15}H_{34}O_2SiNa$ ($M^+$+Na) 297.2226, measured 297.2191.

(c) Oxidation of the hydroxy compound 4. (S)-6-(tert-Butyldimethylsilyloxy)-2,6-dimethyl-heptanal (5). To a solution of NMO (0.3 g, 2.6 mmol) in $CH_2Cl_2$ (11 mL) were added 4 Å molecular sieves (1.65 g) and the mixture was stirred at room temperature for 15 min. Then was added TPAP (30 mg, 0.08 mmol) and a solution of the alcohol 4 (0.3 g, 1.09 mmol) in $CH_2Cl_2$ (1.2 mL). The resultant dark mixture was stirred for 30 min, filtered through a silica Sep-Pak (5 g) and evaporated. The oily residue was dissolved in hexane, applied on a silica Sep-Pak cartridge (5 g) and washed with hexane/AcOEt (98:2) to yield an oily aldehyde 5 (253 mg, 85%).

5: $[\alpha]^{24}_D$+14.6° (c 0.88, $CHCl_3$); $^1H$ NMR (200 Hz, $CDCl_3$) δ 0.06 [6H, s, $Si(CH_3)_2$], 0.85 (9H, s, Si-t-Bu), 0.92 (3H, d, J=6.8 Hz, CH—$CH_3$), 1.17 [6H, s, $C(CH_3)_2$], 2.35 (1H, m, $CH_3CH$), 9.62 (1H, d, J=1.9 Hz, CHO); $^{13}C$ NMR (50 MHz) δ −2.08 [$Si(CH_3)_2$], 13.25 (CH—$CH_3$), 18.07 [$SiC(CH_3)_2$], 21.58 ($CH_2$—$CH_2$—$CH_2$), 25.80 [$SiC(CH_3)_3$], 29.76 and 29.80 [$2\times C(CH_3)_2$], 31.02 ($CH_2CH_2CH_2$), 44.96 ($CH_2CH_2CH_2$), 46.34 (CH—$CH_3$), 73.24 [$C(CH_3)_2$], 205.31 (CHO); HRMS (ESI) exact mass calcd for $C_{15}H_{32}O_2Si$Na ($M^+$+Na) 295.2069, measured 295.2090.

(d) Preparation of the phosphono ester 6. 2-[P,P-Bis(2',2',2'-trifluoroethyl)phosphono]-4-(tert-butyldimethylsilyloxy)-butyric acid methyl ester (6). To a suspension of NaH (60%, 730 mg; washed with hexane) in anhydrous DMF (6.6 mL) at 0° C. was slowly added a solution of $(F_3CCH_2O)_2POCH_2COOCH_3$ (5 g, 15.7 mmol) in anhydrous DMF (6.6 mL). The mixture was stirred at room temperature for 1.5 h and a solution of $Br(CH_2)_2OTBS$ (8.4 mL, 9.3 g, 39.2 mmol) was added in a freshly distilled HMPA (6.8 mL, 39.2 mmol). After stirring at room temperature for 48 h, the reaction mixture was diluted with ethyl acetate and poured into water. The organic phase was separated and the water layer was extracted with ethyl acetate. The combined organic extracts were washed with water, dried ($MgSO_4$) and evaporated. The oily residue was purified by column chromatography on silica gel using hexane/AcOEt (98.5:1.5) as an eluent to yield a crystalline product 6 (2.3 g, 30%).

6: $^1H$ NMR (200 MHz, $CDCl_3$) δ 0.03 [6H, s, $Si(CH_3)_2$], 0.87 [9H, s, Si-t-Bu], 0.92 (3H, d, J=6.8 Hz, CH—$CH_3$), 2.08 (1H, m, one of $CH_2CH_2CH$), 2.21 (1H, m, one of $CH_2CH_2CH$), 3.39 and 3.44 (1H and 1H, each dd, J=10.5, 3.5 Hz, PCHC=O), 3.60 and 3.72 (1H and 1H, each m, $CH_2OTBS$), 3.77 (3H, $COOCH_3$), 4.42 (4H, m, $2\times CH_2OP$); HRMS (ESI) exact mass calcd for $C_{15}H_{28}F_6O_6SiP$ ($M+H^+$) 477.1314, measured 477.1297.

(e) Still-Gennari reaction of the aldehyde 5 with the phosphono ester 6. (S)-8-(tert-Butyldimethylsilyloxy)-2-[2'-(tert-butyldimethylsilyloxy)etyl]-4,8-dimethyl-non-2-enoic acid methyl ester (7). To a solution of phosphono ester 6 (1 g, 2.12 mmol) and 18-crown-6 (2.5 g, 92.5 mmol) in anhydrous THF (50 mL) at −30° C. was dropwise added KHMDS (0.5 M in toluene, 4.25 mL, 2.12 mmol). After stirring for 15 min., the mixture was cooled to −40° C. and a solution of the aldehyde 5 (288 mg, 1.06 mmol) in anhydrous THF (6.3 mL) was added. The mixture was stirred for 2 h at −40° C., 1 h at −30° C., 1 h at −20° C., 1 h at 0° C. and finally for 18 h at room temperature. Saturated $NH_4Cl$ was added and the mixture was extracted with ethyl acetate. The organic phase was dried ($MgSO_4$) and evaporated. The oily residue was purified by column chromatography on silica gel using hexane/AcOEt (95:5) as an eluent providing an isomeric mixture 7 (512 mg, 100%).

7: $^1H$ NMR (200 Hz, $CDCl_3$) δ 0.04 and 0.06 [6H and 6H, each s, $2\times Si(CH_3)_2$], 0.83 and 0.89 (9H and 9H, each s, $2\times$Si-t-Bu), 1.00 (3H, d, J=6.6 Hz, CH—$CH_3$), 1.16 [6H, s, $C(CH_3)_2$], 2.56 (2H, t, J=7.2 Hz, $CH_2C$=C), 3.62 (2H, t, J=7.2 Hz, $CH_2OTBS$), 3.72 (3H, s, $COOCH_3$), 6.62 (1H, d, J=10.2 Hz, C=CH); HRMS (ESI) exact mass calcd for $C_{26}H_{54}O_4Si_2Na$ ($M^+$+Na) 509.3438, measured 509.3458.

(f) Double bond hydrogenation in compound 7 (SCHEME II). (S)-8-(tert-Butyldimethylsilyloxy)-2-[2'-(tert-butyldimethylsilyloxy)etyl]-4,8-dimethyl-nonanoic acid methyl ester (8). To a solution of the ester 7 (158 mg, 0.32 mmol) in anhydrous methanol (8 mL) was added $PtO_2$ (50 mg, 0.22 mmol) at room temperature. The mixture was stirred for 5 days in hydrogen atmosphere, and each day 3 portions of $PtO_2$ (30 mg) were added. The mixture was filtered, the solvent evaporated and the oily residue was purified on silica Sep-Pak (2 g). Elution with hexane/AcOEt (9:1) yielded an oily mixture of products which were separated by HPLC (9.4 mm×25 cm Zorbax-Sil column, 4 mL/min) using a hexane/ethyl acetate (99.65:0.35) solvent system. The isomeric esters 8 (45 mg, 28%; 33% based on recovered substrate) were collected at $R_V$ 104 mL, and the unreacted olefinic compound (E-isomer, 23 mg) was collected at $R_V$ 124 mL.

8: $^1$H NMR (400 Hz, CDCl$_3$) δ 0.03 and 0.05 [6H and 6H, each s, 2×Si(CH$_3$)$_2$], 0.85 and 0.89 (9H and 9H, each s, 2×Si-t-Bu), 1.00 (3H, d, J=6.6 Hz, CH—CH$_3$), 1.17 [6H, s, C(CH$_3$)$_2$], 2.64 (1H, m, CHCOOCH$_3$), 3.59 (2H, m, CH$_2$OTBS), 3.66 (3H, s, COOCH$_3$); HRMS (ES) exact mass calcd for C$_{26}$H$_{56}$O$_4$NaSi$_2$ (M$^+$+Na) 511.3615, measured 511.3600.

(g) Methylation of the ester 8. (S)-8-(tert-Butyldimethylsilyloxy)-2-[2'-(tert-butyldimethylsilyloxy)etyl]-2,4,8-trimethyl-nonanoic acid methyl ester (8). To a solution of diisopropyloamine (85 μL, 0.56 mmol) in anhydrous THF (0.5 mL) was added n-BuLi (1.6 M in cyclohexane, 350 μL, 0.56 mmol) under argon at −20° C. The mixture was stirred for 20 min at −20° C., cooled to −78° C. and a solution of MeI (54 μL, 0.84 mmol) in freshly distilled HMPA (195 μL) was then added. Stirring was continued at −78° C. for 3 h, then the mixture was allowed to warm up to the room temperature and the stirring was continued for 17 h. The mixture was poured into water and extracted with ethyl acetate. The combined organic layers were washed with water, dried (MgSO$_4$) and evaporated. The oily residue was purified on silica Sep-Pak (2 g). Elution with hexane/AcOEt (9:1) gave an oily product 9 (62 mg, 86%).

9: $^1$H NMR (500 Hz, CDCl$_3$) δ 0.03 and 0.05 [6H and 6H, each s, 2×Si(CH$_3$)$_2$], 0.77 (3H, d, J=6.0 Hz, CHCH$_3$), 0.85 and 0.88 (9H and 9H, each s, 2×Si-t-Bu), 1.16 (3H, s 2-CH$_3$), 1.17 [6H, s, C(CH$_3$)$_2$], 3.58 (2H, m, CH$_2$OTBS), 3.64 (3H, s, COOCH$_3$); HRMS (ESI) exact mass calcd for C$_{27}$H$_{59}$O$_4$Si$_2$ (M+H$^+$) 503.3952, measured 503.3958.

(h) Reduction of the ester 9. (S)-8-(tert-Butyldimethylsilyloxy)-2-[2'-(tert-butyldimethylsilyloxy)etyl]-2,4,8-trimethyl-nonan-1-ol (10). To a stirred solution of the ester 9 (32 mg, 0.06 mmol) in toluene/CH$_2$Cl$_2$ (2:1, 1 mL) was added at −78° C. diisobutylaluminium hydride (1.5 M in toluene, 0.27 mL, 0.39 mmol). Stirring was continued at −78° C. for 3 h, and the mixture was quenched by adding 2 M potassium sodium tartrate and diluted HCl. The mixture was extracted with ethyl acetate, the organic extracts were washed with water, dried (MgSO$_4$) and evaporated. The oily residue was purified on silica Sep-Pak (2 g). Elution with hexane/AcOEt (95:5) gave an oily alcohol 10 (31 mg, 100%).

10: $^1$H NMR (500 Hz, CDCl$_3$) δ 0.06 and 0.09 [6H and 6H, each s, 2×Si(CH$_3$)$_2$], 0.93 (3H, d, J=6.8 Hz, CHCH$_3$), 0.88 (3H, s, CCH$_3$), 0.85 and 0.90 (9H and 9H, each s, 2×Si-t-Bu), 1.17 [6H, s, C(CH$_3$)$_2$], 3.30 and 3.62 (1H and 1H, each m, CH$_2$OH), 3.58 (2H, m, CH$_2$OTBS); HRMS (ESI) exact mass calcd for C$_{26}$H$_{58}$O$_3$NaSi$_2$ (M$^+$+Na) 497.3822, measured 497.3829.

(i) Reaction of the alcohol 10 with TDCI. Imidazole-1-carbothioic acid O-[(S)-8-(tert-butyldimethylsilyloxy)-2-[2'-(tert-butyldimethylsilyloxy)etyl]-2,4,8-trimethyl-nonyl]ester (11). To a solution of the alcohol 10 (60 mg, 0.13 mmol) in anhydrous THF (5 mL) was added 1,1'-thiocarbonyl-di-imidazole (150 mg, 0.84 mmol). The mixture was stirred at 75° C. for 6 h and at room temperature for 16 h. Solvent was evaporated and the oily residue was purified on silica Sep-Pak (2 g). Elution with hexane/AcOEt (95:5) yielded an oily thioester 11 (70 mg, 94%).

11: $^1$H NMR (500 Hz, CDCl$_3$) δ 0.05 and 0.06 [6H and 6H, each s, 2×Si(CH$_3$)$_2$], 0.93 (3H, d, J=6.6 Hz, CHCH$_3$), 0.84 and 0.87 (9H and 9H, each s, 2×Si-t-Bu), 1.07 (3H, s, CCH$_3$), 1.16 [6H, s, C(CH$_3$)$_2$OSi], 1.28 (2H, t, J=7.2 Hz), 3.72 (2H, t, J=6.6 Hz, CH$_2$OTBS), 4.44 (2H, m, CH$_2$OCS), 7.05, 7.63 and 8.35 (each 1H, each s, Ar—H); $^{13}$C NMR (125 MHz) δ −5.41 and −2.09 [Si(CH$_3$)$_2$], 18.21 [SiC(CH$_3$)$_3$], 21.67 (CH$_2$—CH$_2$—CH$_2$), 22.43 (CH—CH$_3$), 22.79 (C—CH$_3$), 25.81 and 25.90 [2×SiC(CH$_3$)$_3$], 28.29 (CH—CH$_3$), 29.73 i 29.79 [2×C (CH$_3$)$_2$], 36.97 [C—(CH$_3$)(CH$_2$O)], 40.07 (CH$_2$), 40.32 (CH$_2$), 45.17 (CH$_2$), 45.29 (CH$_2$), 59.29 (CH$_2$OTBS), 73.37 [OC(CH$_3$)$_2$], 117.63, 130.76 and 184.08 (Ar); HRMS (ESI) exact mass calcd for C$_{30}$H$_{60}$O$_3$N$_2$SNaSi$_2$ (M$^+$+Na) 607.3761, measured 607.3761.

(j) Reduction of compound 11. (S)-1,9-Bis(tert-butyldimethylsilyloxy)-3,3,5,9-tetramethyl-decane (12). To a refluxing solution of compound 11 (60 mg, 0.1 mmol) and AIBN (2.5 mg, 0.015 mmol) in anhydrous toluene (3 mL) was dropwise added Bu$_3$SnH (54 μL, 0.2 mmol) during 1 h. The mixture was stirred at 120° C. for 2 h and for 17 h at room temperature. Solvents were evaporated and the oily residue was applied on a silica Sep-Pak (2 g). Elution with hexane/AcOEt (99.8:0.2) yielded an oily diether 12 (22.7 mg, 48%).

12: [α]$^{24}_D$ −0.8° (c 1.1, CHCl$_3$); $^1$H NMR (400 Hz, CDCl$_3$) δ 0.05 and 0.06 [6H and 6H, each s, 2×Si(CH$_3$)$_2$], 0.85 and 0.89 [9H and 9H, each s, 2×Si-t-Bu], 0.88 and 0.90 [3H and 3H, each s, C(CH$_3$)$_2$], 0.91 (3H, d, J=6.6 Hz, CHCH$_3$), 1.17 [6H, s, C(CH$_3$)$_2$OSi], 1.48 (2H, t, J=7.7 Hz), 3.66 (2H, t, J=7.7 Hz, CH$_2$OTBS); $^{13}$C NMR (100 MHz) δ −5.21 and −2.06 [Si(CH$_3$)$_2$], 18.08 and 18.32 [SiC(CH$_3$)$_3$], 21.82 (CH$_2$—CH$_2$—CH$_2$), 22.65 (CH—CH$_3$), 25.84 and 25.99 [2×SiC(CH$_3$)$_3$], 27.73 and 27.77 [2×C(CH$_3$)$_2$], 28.75 (CH—CH$_3$), 29.82 and 29.85 [2×OC(CH$_3$)$_2$], 32.92 [C(CH$_3$)$_2$], 40.26 (CH$_2$), 45.18 (CH$_2$), 45.30 (CH$_2$), 50.05 (CH$_2$), 60.20 (CH$_2$OTBS), 73.61 [OC(CH$_3$)$_2$]; HRMS (ESI) exact mass calcd for C$_{26}$H$_{58}$O$_2$NaSi$_2$ (M$^+$+Na) 481.3873, measured 481.3856.

(k) Deprotection of a primary hydroxyl in compound 12. (S)-9-(tert-Butyldimethylsilyloxy)-3,3,5,9-tetramethyl-decan-1-ol (13). To a solution of diether 12 (30 mg, 65 μmol) in anhydrous THF (10 mL) was added tetrabutylammonium fluoride (1.0 M in THF, 130 μL, 130 μmol). The mixture was stirred under argon at room temperature for 18 h, poured into brine and extracted with ethyl acetate. Organic extracts were washed with brine, dried (MgSO$_4$) and evaporated. The oily residue was purified on a silica Sep-Pak (2 g). Elution with hexane/AcOEt (9:1) gave an oily alcohol 13 (23 mg, 100%).

13: [α]$^{24}_D$ −0.6° (c 1.15, CHCl$_3$); $^1$H NMR (400 Hz, CDCl$_3$) δ 0.05 [6H, s, Si(CH$_3$)$_2$], 0.85 [9H, s, Si-t-Bu], 0.90 (6H, s, 2×CH$_3$), 0.91 (3H, d, J=6.6 Hz, CHCH$_3$), 1.17 [6H, s, C(CH$_3$)$_2$OSi], 3.70 (2H, t, J=7.7 Hz, CH$_2$OH); $^{13}$C NMR (100 MHz) δ −2.08 [Si(CH$_3$)$_2$], 18.09 [SiC(CH$_3$)$_3$], 21.04 (CH—CH$_3$), 21.80 (CH$_2$—CH$_2$—CH$_2$), 25.83 [SiC(CH$_3$)$_3$], 27.73 and 27.77 [2×C(CH$_3$)$_2$], 28.77 (CH—CH$_3$), 29.84 [OC(CH$_3$)$_2$], 32.98 [C(CH$_3$)$_2$], 40.22 (CH$_2$), 45.28 (CH$_2$), 45.33 (CH$_2$), 49.98 (CH$_2$), 59.92 (CH$_2$OH), 73.48 [OC(CH$_3$)$_2$]; HRMS (ES) exact mass calcd for C$_{20}$H$_{44}$O$_2$NaSi (M$^+$+Na) 367.3008, measured 367.3000.

(l) Oxidation of the alcohol 13. (S)-9-(tert-Butyldimethylsilyloxy)-3,3,5,9-tetramethyl-decanal (14). To a solution of NMO (19 mg, 0.16 mmol) in CH$_2$Cl$_2$ (0.7 mL) were added 4 Å molecular sieves (100 mg) and the mixture was stirred at room temperature for 15 min. Then was added TPAP (1.4 mg, 3.72 μmol) and a solution of the alcohol 14 (23 mg, 67 μmol) in CH$_2$Cl$_2$ (200 μL). The resultant dark mixture was stirred for 2 h, filtered through a silica Sep-Pak (2 g) and evaporated. The oily residue was dissolved in hexane, applied on a silica Sep-Pak cartridge (2 g) and washed with hexane/AcOEt (99:1) yielding an oily aldehyde 15 (16 mg, 70%).

15: [α]$^{24}_D$ −0.6° (c 0.80, CHCl$_3$); $^1$H NMR (400 Hz, CDCl$_3$) δ 0.05 [6H, s, Si(CH$_3$)$_2$], 0.85 [9H, s, Si-t-Bu], 0.93 (3H, d, J=6.6 Hz, CHCH$_3$), 1.06 (6H, s, 2×CH$_3$), 1.17 [6H, s, C(CH$_3$)$_2$], 2.26 (2H, m, CH$_2$CHO), 9.85 (1H, t, J=3.14 Hz);

13C NMR (100 MHz) δ −2.08 [Si(CH$_3$)$_2$], 18.10 [SiC(CH$_3$)$_3$], 21.74 (CH—CH$_3$), 22.52 (CH$_2$—CH$_2$—CH$_2$), 25.83 [SiC(CH$_3$)$_3$], 27.64 and 29.84 [C(CH$_3$)$_2$], 28.86 (CH—CH$_3$), 34.20 [C—(CH$_3$)$_2$], 40.02 (CH$_2$), 45.22 (CH$_2$), 45.22 (CH$_2$), 50.15 (CH$_2$), 55.56 (CH$_2$OH), 73.44 [C(CH$_3$)$_2$], 203.91 (CHO); HRMS (ES) exact mass calcd for C$_{20}$H$_{42}$O$_2$NaSi (M$^+$+Na) 365.2852, measured 365.2840.

(m) Wittig-Horner reaction of aldehyde 14 with phosphine oxide 15 and deprotection of hydroxy groups. (1R,3R)-5-[(E)-(S)-11'-hydroxy-5',5',7',11'-tetramethyl-dodec-2'-enylidene]-2-methylene-cyclohexane-1,3-diol (16,13Me$_2$) and (1R,3R)-5-[(Z)-(S)-11'-hydroxy-5',5',7',11'-tetramethyl-dodec-2'-enylidene]-2-methylene-cyclohexane-1,3-diol (17, 13-Me$_2$-C). To a solution of phosphine oxide 15 (83 mg, 141 μmol) in anhydrous THF (0.8 mL) at −78° C. was slowly added phenyllithium (1.8 M in cyclohexane, 75 μL, 141 μmol) under argon with stirring. The solution turned deep orange. The mixture was stirred at −78° C. for 20 min., and a precooled (−78° C.) solution of the aldehyde 14 (16 mg, 47 μmol) in anhydrous THF (300 μL) was slowly added. The mixture was stirred at −78° C. under argon for 3 h and at 6° C. for 16 h. Ethyl acetate and water were added, and the organic phase was separated, washed with brine, dried (MgSO$_4$) and evaporated. The oily residue was purified on a silica Sep-Pak cartridge (2 g). Elution with hexane/AcOEt (99.8:0.2) yielded a mixture of isomeric protected vitamin D analogs (17 mg, 52%). The major product was identified as (1R,3R)-1,3-bis-(tert-butyldimethylsilyloxy)-5-[(E)-(S)-11'-(tert-butyldimethylsilyloxy)-5',5',7',11'-tetramethyl-dodec-2'-enylidene]-2-methylene-cyclohexane (16).

(16): UV (hexane) λ$_{max}$ 237.0, 244.0, 276.5 nm; $^1$H NMR (400 Hz, CDCl$_3$; vitamin D numbering) δ 0.027 and 0.037 [3H and 3H, each s, 2×Si(CH$_3$)$_2$], 0.058 and 0.064 [6H and 6H, each s, 2×(SiCH$_3$)$_2$], 0.85, 0.87 and 0.89 [3×9H, each s, 3×Si-t-Bu], 0.85-0.91 (9H, overlapped with Si-t-Bu, 21- and 13-Me$_2$), 1.17 [6H, s, 26- and 27-H$_3$], 1.96 (1H, m, 20-H), 2.15 (1H, dd, J=12.5, 8.0 Hz, 4β-H), 2.40 (3H, m, 4α-, 10α- and 10β-H), 4.42 (2H, m, 1β- and 3α-H), 4.93 and 4.96 (1H and 1H, each s, C=CH$_2$), 5.64 (1H, dt, J=14.7, 7.6 Hz, 8-H), 5.92 (1H, d, J=10.8 Hz, 6-H), 6.21 (1H, dd, J=14.7, 10.8 Hz, 7-H); $^{13}$C NMR (100 MHz) δ −4.98, −4.87 and −2.06 [3×Si(CH$_3$)$_2$], 18.11, 18.14 and 18.23 [3×SiC(CH$_3$)$_3$], 21.88 (C-20), 22.78 (C-23), 25.74, 25.80 and 25.86 [3×SiC(CH$_3$)$_3$], 27.36 and 27.40 (13-Me$_2$), 28.91 (C-13), 29.94 (C-26 and C-27), 34.03 (C-21), 38.96 (C-22), 40.34 and 45.40 (C-4 and C-10), 46.69 (C-24), 47.23 (C-14), 49.64 (C-17), 71.82 and 72.34 (C-1 and C-3), 73.52 (C-25), 106.31 (C=CH$_2$), 127.24 (C-6), 128.16 (C-7), 130.22 (C-8), 132.9 (C-5), 152.84 (C-2); HRMS (ES) exact mass calcd for C$_{41}$H$_{82}$O$_3$Si$_3$Na (M$^+$+Na) 729.5470, measured 729.5437. This compound was contaminated with a small quantity of its 7Z-isomer (vitamin D numbering).

To a solution of protected vitamins (17 mg, 24 μmol) in THF (3 mL) and acetonitrile (1 mL) was added MeCN/46% HF (9:1, 4 mL) at room temperature. After stirring for 4 h, a saturated NaHCO$_3$ was added. The racemic mixture was extracted with CH$_2$Cl$_2$, organic extracts were washed with brine, dried (MgSO$_4$) and evaporated. The residue was first purified on a silica Sep-Pak (0.5 g). Elution with hexane/ethyl acetate (1:1) yielded a mixture of deprotected vitamins 16 and 17 (5.2 mg, 63%). Separation of both isomers was achieved by reversed-phase HPLC (9.4 mm×25 cm, Eclipse XDB-C18 column, 3 mL/min) using a methanol/water (85:15) solvent system. Vitamin D analog 16 (4.9 mg) was collected at R$_V$ 30.8 mL and the 7Z-isomer 17 (280 μg) at R$_V$ 32.0 mL.

16: UV (EtOH) λ$_{max}$ 236.5, 243.0, 275.5 nm; $^1$H NMR (400 Hz, CDCl$_3$; vitamin D numbering) δ 0.87 [6H, s, 13-Me$_2$], 0.91 (3H, d, J=6.6 Hz, 21-H$_3$), 1.21 [6H, s, 26- and 27-H$_3$], 2.26 (1H, dd, J=13.2, 6.9 Hz, 4β-H), 2.38 (1H, dd, J=13.3, 7.4 Hz, 10α-H), 2.56 (1H, dd, J=13.2, 4.3 Hz, 4α-H), 2.71 (1H, dd, J=13.3, 4.2 Hz, 10β-H), 4.48 (2H, m, 1β- and 3α-H), 5.09 (2H, s, C=CH$_2$), 5.71 (1H, dt, J=14.7, 7.6 Hz, 8-H), 6.05 (1H, d, J=10.8 Hz, 6-H), 6.27 (1H, dd, J=14.7, 10.8 Hz, 7-H); $^{13}$C NMR (100 MHz) δ 21.85 (C-23), 22.49 (C-21), 27.49 and 27.65 [13-Me$_2$], 28.70 (C-13), 29.26 (C-26 and C-27), 34.54 (C-20), 38.12 (C-22), 40.08 and 45.53 (C-4 and C-10), 44.15 (C-24), 46.31 (C-14), 49.38 (C-17), 70.98 (C-25), 71.13 and 71.43 (C-1 and C-3), 107.89 (C=CH$_2$), 127.41 (C-6), 128.80 (C-7), 131.06 (C-8), 132.14 (C-5), 151.82 (C-2); HRMS (ESI) exact mass calcd for C$_{23}$H$_{40}$O$_3$Na (M$^+$+Na) 387.2875, measured 387.2859.

17: UV (EtOH) λ$_{max}$ 238.5, 244.0 nm; $^1$H NMR (500 Hz, CDCl$_3$; vitamin D numbering) δ 0.89 and 0.90 [3H and 3H, each s, 13-Me$_2$], 0.91 (3H, d, J=6.6 Hz, 21-H$_3$), 1.21 (6H, s, 26- and 27-H$_3$), 2.08 and 2.12 (1H and 1H, each dd, J=13.2, 7.5 Hz, 14-H$_2$), 2.32 (1H, dd, J=13.1, 6.7 Hz, 4β-H), 2.39 (1H, dd, J=13.2, 7.6 Hz, 10α-H), 2.60 (1H, dd, J=13.1, 4.2 Hz, 4α-H), 2.74 (1H, dd, J=13.2, 4.2 Hz, 10β-H), 4.49 (2H, m, 1β- and 3α-H), 5.11 (2H, s, C=CH$_2$), 5.56 (1H, dt, J=9.6, 7.5 Hz, 8-H), 6.33 (2H, m, 6- and 7-H); HRMS (ESI) exact mass calcd for C$_{23}$H$_{40}$O$_3$Na (M$^+$+Na) 387.2875, measured 387.2876.

SCHEME 1

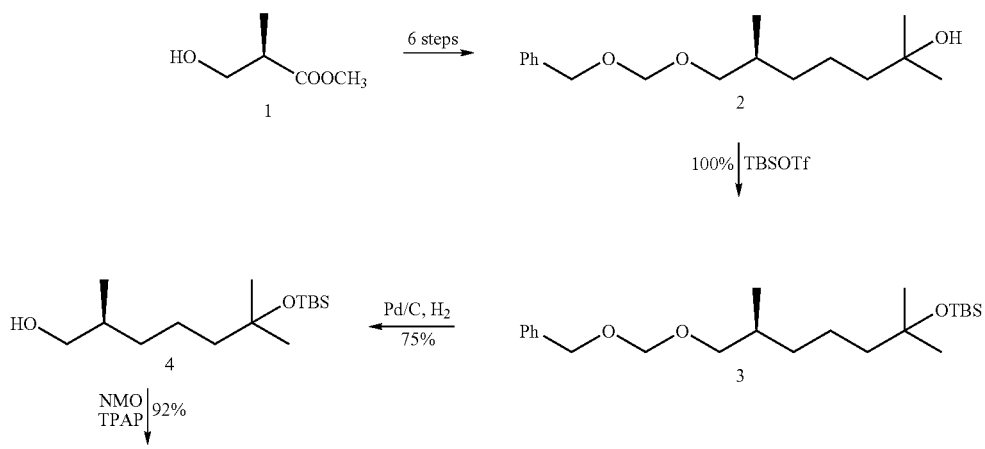

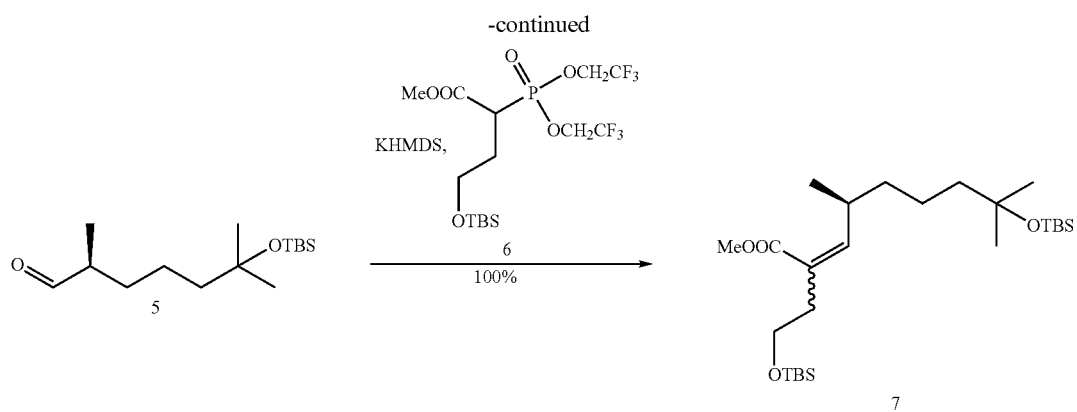
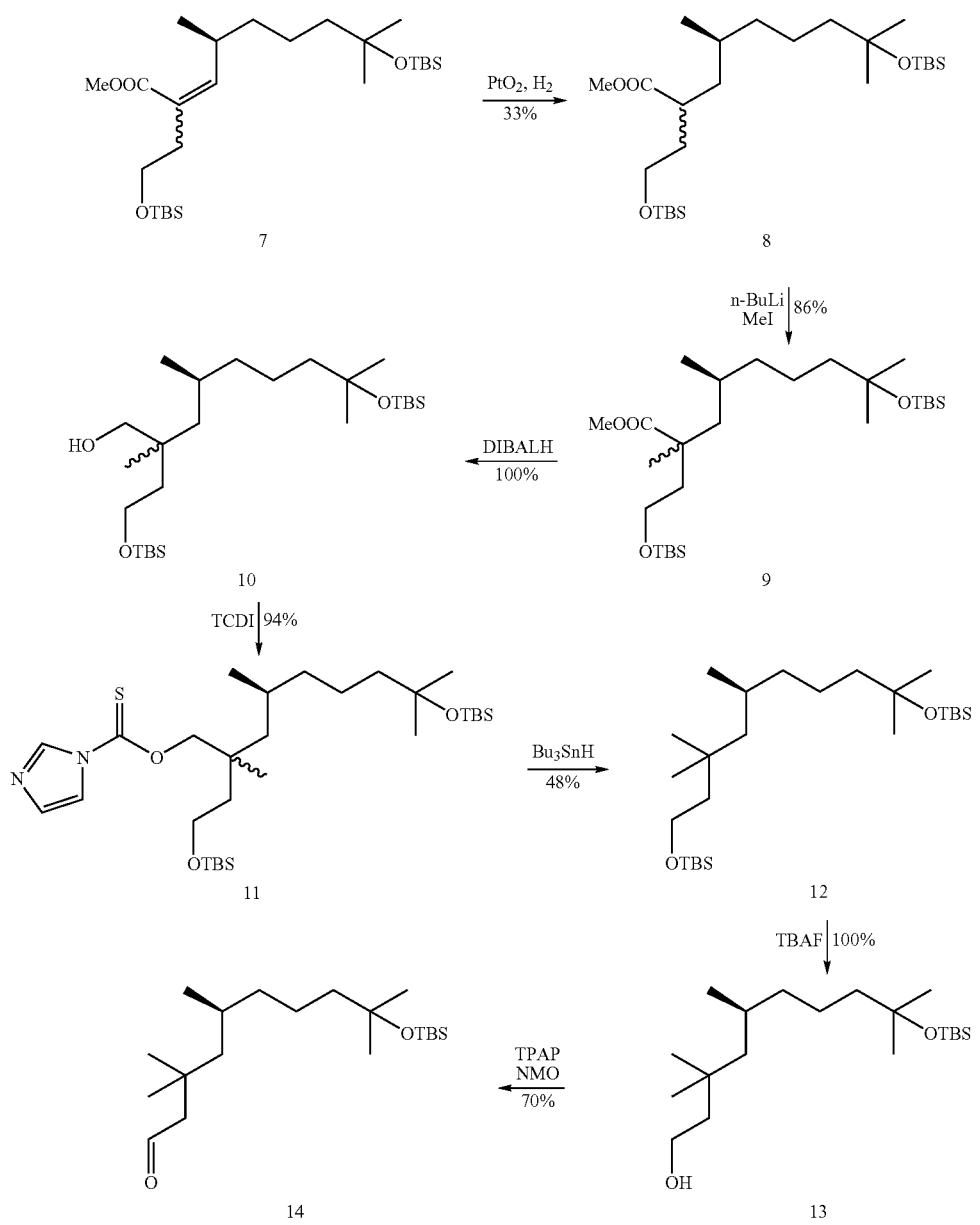
SCHEME 2

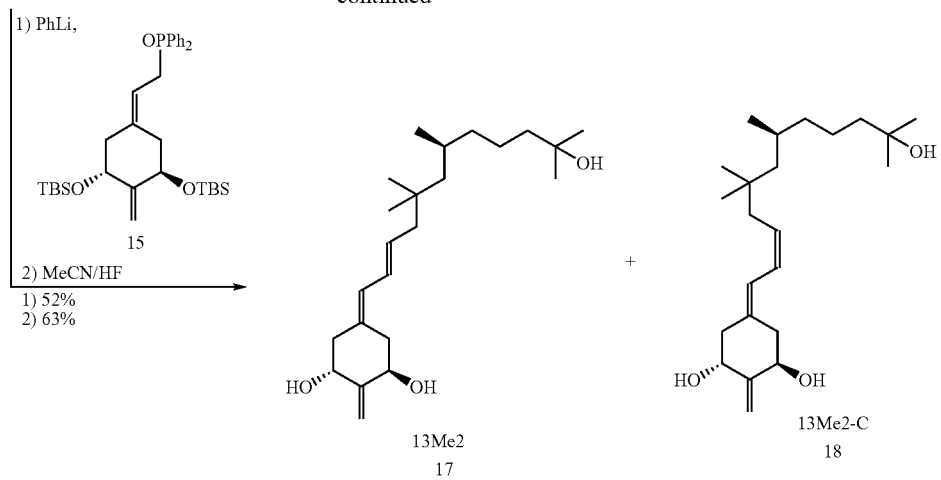

13Me$_2$ binds the VDR with one log less affinity compared to the native hormone. Consistent with the lower binding activity, the differentiation and transcription activities are also lower than 1.25(OH)$_2$D$_3$ by approximately one log. Although 13Me$_2$ is less potent in vitro than 1.25(OH)$_2$D$_3$, it exhibits insignificant activity on intestinal calcium transport and/or bone calcium mobilization.

Experimental Methods. Vitamin D Receptor Binding. Test Material Protein Source. Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK50 (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs. Unlabeled ligands were dissolved in ethanol, and the concentrations determined using UV spectrophotometry (1.25(OH)$_2$D$_3$: molar extinction coefficient=18,200 and $\lambda_{max}$=265 nm; Analog: molar extinction coefficient=30,200 and $\lambda_{max}$=243 nm). Radiolabeled ligand ($^3$H-1.25(OH)$_2$D$_3$, ~159 Ci/mmole) was added in ethanol at a final concentration of 1 nM.

Assay Conditions. Radiolabeled and unlabeled ligands were added to 100 μl of the diluted protein at a final ethanol concentration of <10%, mixed and incubated overnight on ice to reach binding equilibrium. The following day, 100 μl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation. Test Material. Study Drugs. The study drugs were dissolved in ethanol and the concentrations determined using UV spectrophotometry. Serial dilutions were prepared so that a range of drug concentrations could be tested without changing the final concentration of ethanol (<0.2%) present in the cell cultures.

Cells. Human promyelocytic leukemia (HL-60) cells were grown in RPMI-1640 medium containing 10% fetal bovine serum. The cells were incubated at 37° C. in the presence of 5% CO$_2$.

Assay Conditions. HL-60 cells were plated at 1.2×10$^5$ cells/ml. Eighteen hours after plating, cells in duplicate were treated with drug. Four days later, the cells were harvested and a nitro blue tetrazolium reduction assay was performed. (Collins et al., 1979, *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay. Transcription activity was measured in ROS 17/2.8 (bone) cells that were stably transfected with a 24-hydroxylase (24OHase) gene promoter upstream of a luciferase reporter gene. (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization Activity. Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

TABLE 1

COMEDOLYTIC EFFECT OF DAILY TOPICAL APPLICATION OF 1,25-DIHYDROXYVITAMIN D3 AND 13Me₂ TO THE RHINO MOUSE

| Compound* | Comedone Area (% Vehicle)** | Dose (nmol/kg) | N |
|---|---|---|---|
| 1,25(OH)₂D₃ | 187 ± 30 | 6.0 | 6 |
| 13Me₂ | 26 ± 3 | 217 | 6 |

*All compounds were applied topically on a daily basis for ca. 3 weeks in vehicle comprised of 70 vol % ethanol and 30 vol % propylene glycol.
**Values are mean + standard error of the mean

TABLE 2

PREDICTIVE HUMAN TOPICAL DOSING RANGE

| COMPOUND | TOPICAL DOSING RANGE |
|---|---|
| 13Me₂ | 36 mg to 11 ng/kg$_{BW}$/day |

Rhino mice were used to topically test the compounds and compositions of the invention. The Rhino mouse is a well-established animal model used to study the comedolytic effects of anti-acne agents including retinoids. (See Boulcier M et al., 1990, Experimental Models in Skin Pharmacology, *In Pharmacological Reviews* 42:127-154). The Rhino mouse model was used to study the therapeutic potential of 13Me₂.

Animals and dose administration. Rhino mice were enrolled in the study at 6-8 weeks of age and were dosed daily via the topical route. The mice were weighed three times per week and doses were adjusted weekly based on body weight. The topical formulations were applied to the back of the animal in a maximum volume of 100 μL. The topical formulations were made by mixing the 13Me₂ with a topical carrier comprising 70 vol % ethanol and 30 vol % propylene glycol, as indicated. The topical vehicle control was the vehicle carrier solution matched to the formulation containing API and vehicle carrier. Mice were sacrificed 72 hours after the final topical dose. At sacrifice, the dorsal skin was collected for histology studies.

Comedolytic effect. The extent of the comedolytic effect (i.e., efficacy) was assessed by measuring the average area of the comedones, whereby the smaller the area, the larger the effect. The comedone area was determined by histological analysis of tissue sections based upon lab methods. Skin was fixed overnight in 4% paraformaldehyde at 4° C. with gentle agitation, and dehydrated the next day into 100% methanol.

Samples were embedded in paraffin and a total of nine 10μ sections 150μ apart were prepared from each Rhino mouse. Five of the nine sections were digitally imaged (6× magnification) for comedone analysis using Metamorph Imaging Software (trace function). The perimeter of each comedone on the images taken from the 5 sections was then traced using a Wacom Intuos 3 Graphics Tablet interfaced with the software.

The number of pixels comprising the area of each individual comedone was obtained, and the mean number of pixels per comedone was obtained for each Rhino mouse. For comedones that were completely healed (area=0) a pixel value approaching 0 (<10) was scored. The individual comedone area average for each mouse was then used to calculate the treatment group mean. Results in the figures are expressed in terms of mean±standard error of the mean.

Preparation of topical formulations containing 13Me₂. A concentrated ethanolic stock of 13Me₂ was diluted to a final concentration containing 30 vol % propylene glycol and 70 vol % ethanol as the excipient carrier system. The mixture was thoroughly mixed. The topical dosing formulation delivered a predetermined dosing amount of drug on a per kilogram body weight basis. A 100 μL dose was administered to the back of the mouse. An average weight of 24-30 g/mouse was assumed in dose volume calculations. Dosing volumes were adjusted weekly to deliver the desired predetermined dosing amount of API based on the body weight of each individual animal.

The invention claimed is:

1. A compound having the structure

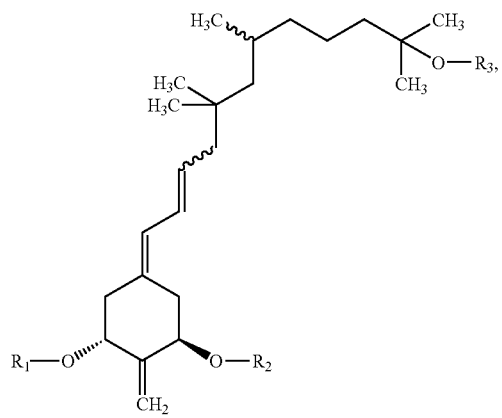

wherein $R_1$ is a member selected from the group consisting of hydrogen and a protecting group, wherein $R_2$ is a member selected from the group consisting of hydrogen and a protecting group, wherein $R_3$ is a member selected from the group consisting of hydrogen and a protecting group, and, wherein each ⁓ is independently ⫽ or ⁄.

2. The compound of claim 1, wherein $R_1$, $R_2$ and $R_3$ are each t-butyldimethylsilyl.

3. The compound of claim 1, wherein $R_1$, $R_2$ and $R_3$ are each hydrogen.

4. The compound of claim 1, wherein the compound is (1R,3R)-5-[(E)-(S)-11'-hydroxy-5',5',7',11'-tetramethyl-dodec-2'-enylidene]-2-methylene-cyclohexane-1,3-diol and/or (1R,3R)-5-[(Z)-(S)-11'-hydroxy-5',5',7',11'-tetramethyl-dodec-2'-enylidene]-2-methylene-cyclohexane-1,3-diol.

5. The compound of claim 1, wherein the compound is (1R,3R)-5-[(E)-(R)-11'-hydroxy-5',5',7',11'-tetramethyl-dodec-2'-enylidene]-2-methylene-cyclohexane-1,3-diol and/or (1R,3R)-5-[(Z)-(R)-11'-hydroxy-5',5',7',11'-tetramethyl-dodec-2'-enylidene]-2-methylene-cyclohexane-1,3-diol.

6. A method of making a compound comprising:

reacting a racemic mixture of an aldehyde reactant having the structure

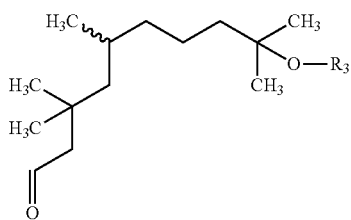

with an allylic phosphine oxide reactant having the structure

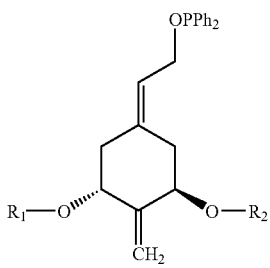

to yield a diastereomeric mixture of a protected compound having the structure

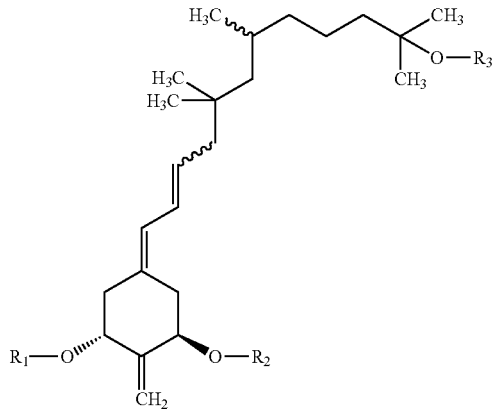

wherein $R_1$, $R_2$, and $R_3$ are each a protecting group, and, wherein each ⌇ is independently ⌀ or ⁄.

7. The method of claim 6, wherein $R_1$, $R_2$ and $R_3$ are each t-butyldimethylsilyl.

8. The method of claim 6, further comprising deprotecting the protected compound to yield a diastereomeric mixture of a deprotected compound having the structure

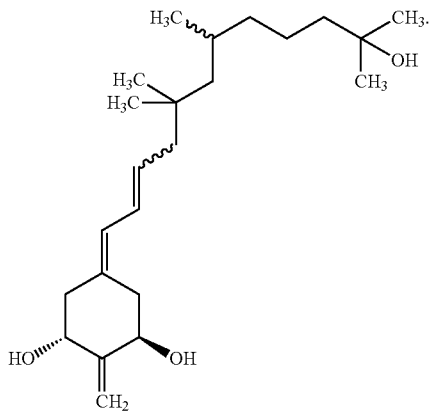

9. The method of claim 8, wherein the diastereomeric mixture of the deprotected compound comprises (1R,3R)-5-[(E)-(S)-11'-hydroxy-5',5',7',11'-tetramethyl-dodec-2'-enylidene]-2-methylene-cyclohexane-1,3-diol and (1R,3R)-5-[(Z)-(S)-11'-hydroxy-5',5',7',11'-tetramethyl-dodec-2'-enylidene]-2-methylene-cyclohexane-1,3-diol.

10. The method of claim 8, wherein the diastereomeric mixture of the deprotected compound comprises (1R,3R)-5-[(E)-(R)-11'-hydroxy-5',5',7',11'-tetramethyl-dodec-2'-enylidene]-2-methylene-cyclohexane-1,3-diol and (1R,3R)-5-[(Z)-(R)-11'-hydroxy-5',5',7',11'-tetramethyl-dodec-2'-enylidene]-2-methylene-cyclohexane-1,3-diol.

11. A method of making a compound comprising:
reacting an enantiomer of an aldehyde reactant having the structure

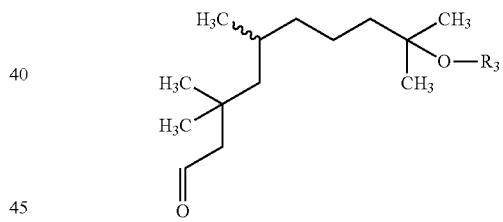

with an allylic phosphine oxide reactant having the structure

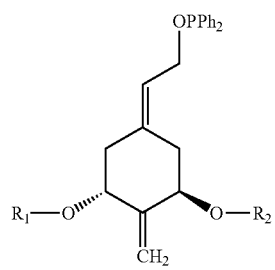

to yield a mixture of geometric isomers of a protected compound having the structure

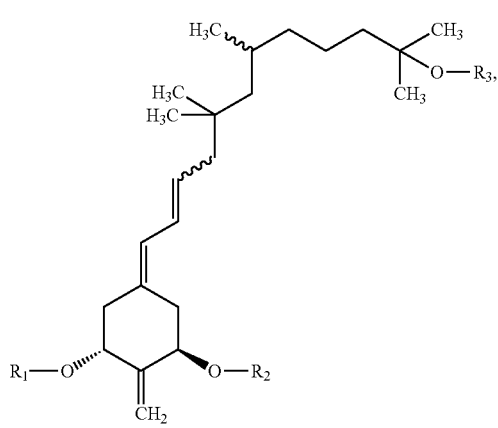

wherein $R_1$, $R_2$, and $R_3$ are each a protecting group, and, wherein each ⌇ is independently ⫽⫽⫽ or ∕ , deprotecting the mixture of geometric isomers of the protected compound to yield an isomeric mixture of a deprotected compound having the structure

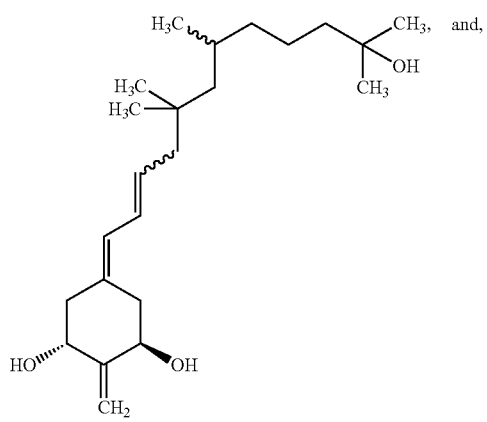

and, separating the mixture of geometric isomers of the deprotected compound to yield the separated isomers of deprotected compound, wherein the deprotecting and separating are performed in either sequence.

12. The method of claim 11, wherein $R_1$, $R_2$ and $R_3$ are each t-butyldimethylsilyl.

13. The method of claim 11, wherein $R_1$, $R_2$ and $R_3$ are each hydrogen.

14. The method of claim 11, wherein the separated isomers of the deprotected compound comprise (1R,3R)-5-[(E)-(S)-11'-hydroxy-5',5',7',11'-tetramethyl-dodec-2'-enylidene]-2-methylene-cyclohexane-1,3-diol and (1R,3R)-5-[(Z)-(S)-11'-hydroxy-5',5',7',11'-tetramethyl-dodec-2'-enylidene]-2-methylene-cyclohexane-1,3-diol.

15. The method of claim 11, wherein the separated isomers of the deprotected compound comprises (1R,3R)-5-[(E)-(R)-11'-hydroxy-5',5',7',11'-tetramethyl-dodec-2'-enylidene]-2-methylene-cyclohexane-1,3-diol and (1R,3R)-5-[(Z)-(R)-11'-hydroxy-5',5',7',11'-tetramethyl-dodec-2'-enylidene]-2-methylene-cyclohexane-1,3-diol.

16. A compound made by any one of the methods of claims 6-15.

17. A topical composition comprising:
a therapeutically effective dose of a compound of any of claims 1-5 and a pharmaceutically suitable carrier system.

18. The topical composition of claim 17, wherein the dose is in the range of 36 mg to 11 ng/$kg_{BW}$/day.

19. The topical composition of claim 17, wherein the topical carrier system comprises in the range of 30-70% ethanol and 30-70% propylene glycol.

20. The topical composition of claim 17, wherein the topical carrier system comprises 70% ethanol and 30% propylene glycol.

21. A method of treating acne comprising topically administering daily or intermittently to a human a topical composition comprising a therapeutically effective dose of a compound of claim 1 and a pharmaceutically suitable carrier system.

22. A method of reducing comedone area comprising topically administering daily or intermittently to a human a topical composition comprising a therapeutically effective dose of a compound of claim 1 and a pharmaceutically suitable carrier system.

23. A method of treating psoriasis comprising topically administering daily or intermittently to a human a topical composition comprising a therapeutically effective dose of a compound of claim 1 and a pharmaceutically suitable carrier system.

24. A method of treating ichthyosis comprising topically administering daily or intermittently-to a human a topical composition comprising a therapeutically effective dose of a compound of claim 1 and a pharmaceutically suitable carrier system.

25. A method of treating photoaging or photodamaged skin comprising topically administering daily or intermittently to a human a topical composition comprising a therapeutically effective dose of a compound of claim 1 and a pharmaceutically suitable carrier system.

26. A method of treating skin cancer comprising topically administering daily or intermittently to a human a topical composition comprising a therapeutically effective dose of a compound of claim 1 and a pharmaceutically suitable carrier system.

27. A compound having the structure

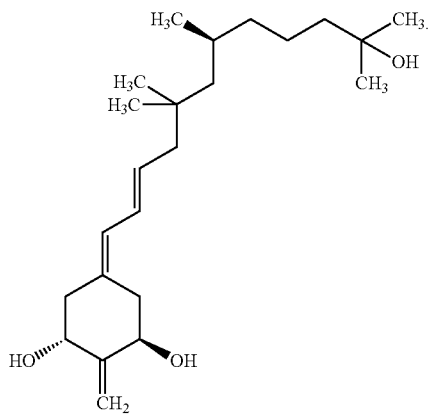

28. A composition comprising:
a therapeutically effective dose of an active pharmaceutical ingredient according to the structure

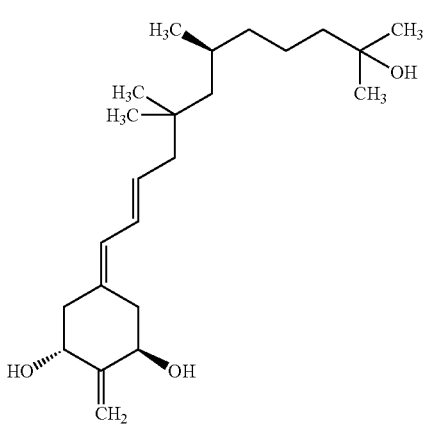

and a pharmaceutically suitable topical carrier system.

29. The topical composition of claim 28, wherein the dose is in the range of 36 mg to 11 ng/kg$_{BW}$/day.

30. The topical composition of claim 28, wherein the topical carrier system comprises in the range of 30-70% ethanol and 30-70% propylene glycol.

31. The topical composition of claim 28, wherein the topical carrier system comprises 70% ethanol and 30% propylene glycol.

32. A method of treating acne comprising topically administering daily or intermittently any one of the topical compositions of claims 28-31 to a human.

33. A method of reducing comedone area comprising topically administering daily or intermittently any one of the topical compositions of claims 28-31 to a human.

34. A method of treating psoriasis comprising topically administering daily or intermittently any one of the topical compositions of claims 28-31 to a human.

35. A method of treating ichthyosis comprising topically administering daily or intermittently any one of the topical compositions of claims 28-31 to a human.

36. A method of treating photoaging or photodamaged skin comprising topically administering daily or intermittently any one of the topical compositions of claims 28-31 to a human.

37. A method of treating skin cancer comprising topically administering daily or intermittently any one of the topical compositions of claims 28-31 to a human.

* * * * *